US008137929B2

(12) United States Patent
Shaw et al.

(10) Patent No.: US 8,137,929 B2

(45) **Date of Patent: *Mar. 20, 2012**

(54) BASIC PROTEIN PURIFICATION TAGS FROM THERMOPHILIC BACTERIA

(75) Inventors: Allan Christian Shaw, Copenhagen (DK); Susanne Bang, Bagsvaerd (DK); Jing Su, Beijing (CN)

(73) Assignee: Novo Nordisk Health Care AG, Zurich (CH)

( * ) Notice: Subject to any disclaimer, the term of this patent is extended or adjusted under 35 U.S.C. 154(b) by 157 days.

This patent is subject to a terminal disclaimer.

(21) Appl. No.: 11/911,563

(22) PCT Filed: Apr. 10, 2006

(86) PCT No.: PCT/EP2006/061493

§ 371 (c)(1), (2), (4) Date: Sep. 3, 2008

(87) PCT Pub. No.: WO2006/108826

PCT Pub. Date: Oct. 19, 2006

(65) Prior Publication Data

US 2009/0306352 A1 Dec. 10, 2009

Related U.S. Application Data

(60) Provisional application No. 60/675,054, filed on Apr. 26, 2005.

(30) Foreign Application Priority Data

Apr. 15, 2005 (DK) ................................ 2005 00549

(51) Int. Cl.
*C12P 21/06* (2006.01)

(52) U.S. Cl. .................... 435/69.1; 435/69.4; 435/69.7; 435/71.1; 435/71.2; 435/68.1

(58) Field of Classification Search ....................... None
See application file for complete search history.

(56) References Cited

U.S. PATENT DOCUMENTS

| | | | |
|---|---|---|---|
| 4,880,911 | A | 11/1989 | Brewer et al. |
| 5,322,930 | A | 6/1994 | Tarnowski et al. |
| 5,532,142 | A | 7/1996 | Johnston et al. |
| 2008/0255025 | A1 | 10/2008 | Ladner |
| 2009/0306352 | A1 | 12/2009 | Shaw et al. |

FOREIGN PATENT DOCUMENTS

| | | |
|---|---|---|
| JP | 2006-096713 | 4/2006 |
| WO | WO 00/06343 | 2/2000 |
| WO | WO 02/18447 A1 | 3/2002 |
| WO | WO 2006/108826 | 10/2006 |

OTHER PUBLICATIONS

Graslund et al (Protein Engineering, 13(10):703-709, 2000).*
Graslund et al (Journal of Chromatography, A 942:157-166, 2002).*
Nelson et al UniProt Accession No. Q9WZW7, publically available Nov. 1, 1999.*
Shin et al (Journal of Biotechnology 62:143-151, 1998).*
Bi et al, Protein Expression and Purification, 2006, vol. 47, pp. 234-240.
Boime, I et al, Database Genese Q, 2001, EBI accession No. GSP: AAE04488.
Boime, I et al, Database Genese Q, 2001, EBI accession No. GSP: AAE04505.
Copeland, A et al, Database Uniprot, 2006, EBI accession No. AOLWU2.
Copeland, A et al, Database Uniprot, 2007, EBI accession No. A6LMW8.
Erfle, V. et al, Database Genese Q, 2004, EBI accession No. GSP: ADO57970.
Henne, A et al, Database Uniprot, 2004, EBI accession No. Q72GV5.
Kuboki, Y et al, Database Genese Q, 2006, EBI accession No. AEH09114.
Kuhlman et al., "Structure and Stability of the N-Terminal Domain of the Ribosomal Protein L9: Evidence for Rapid Two-State Folding", Biochemistry, 1998, No. 37, pp. 1025-1032.
Kuhlman, B et al, Journal of Molecular Biology, 1998, vol. 284, Part 5, pp. 1661-1670.
Machine Translation of JP 2006-096713, published Apr. 13, 2006.
Neumann, M. et al, Database EPO Proteins, 2003, EPOP accession No. AX589447.
Takami, H. et al, Database Uniprot, 2005, EBI accession No. Q5KU74.
Terpe, K, Applied Microbiology and Biotechnology, 2003, vol. 60, Part 5, pp. 523-533.
Non-Final Office Action for U.S. Appl. No. 12/443,694, (filed Mar. 31, 2009 by Shaw et al.) mailed from the USPTO on May 11, 2010.
Notice of Allowance for U.S. Appl. No. 12/443,694, (filed Mar. 31, 2009 by Shaw et al.) mailed from the USPTO on Oct. 20, 2010.
Graslund, T. et al., "Charge Engineering of a Protein Domain to Allow Efficient Ion-Exchange Recovery", Protein Engineering, 2000, vol. 13, No. 10, pp. 703-709.
Graslund, T. et al., "Strategy for Highly Selective Ion-Exchange Capture Using a Charge-Polarizing Fusion Partner", Journal of Chromatography, 2002, vol. 942, No. 1-2, pp. 157-166.
Graslund, T. et al., "Integrated Strategy for Selective Expanded Bed Ion-Exchange Adsorption and Site-Specific Protein Processing Using Gene Fusion Technology", Journal of Biotechnology, 2002, vol. 96, No. 1, pp. 93-102.
Copeland, A et al, 50S Ribosomal Protein L9, Database Uniprot, 2006, EBI accession No. YP873888.1, Nov. 13, 2006.

(Continued)

*Primary Examiner* — Patricia A Duffy
(74) *Attorney, Agent, or Firm* — Teresa Chen

(57) ABSTRACT

The invention is related to a method for purification of recombinant proteins using highly basic proteins from thermophilic bacteria as purification tags for use in a cation-exchange chromatography purification step. The basic proteins may be ribosomal proteins. The recombinant proteins are expressed in eukaryotic or prokaryotic host cells. The purification tag will typically have a pI above about 9 and comprise from about 15 to about 250 amino acid residues.

12 Claims, 11 Drawing Sheets

OTHER PUBLICATIONS

Copeland, A et al, Ribosomal Protein L9, Database Uniprot, 2007, EBI accession No. ABR31269.1, Jun. 26, 2007.

Elke, et al, Biological Chemistry Hoppe-Seyler, The Amino Acid Sequences Of The Bacillus Stearo Thermophilus Ribosomal Protein SS17 and S21 and Their Comparison to Homologus Proteins od Other Ribosomes, 1991, vol. 372, pp. 955-961.

Henne, A et al, 50S Ribosomal Protein L9, Database Uniprot, 2004, EB1 accession No. Q72GV5.1, Jul. 5, 2004.

Machine Translation of JP 2006-096713, published Apr. 13, 2006.

Kazutomo, et al, Dictionary of Biochemistry, 2002, vol. 3, p. 1489.

Klenk HP, et al, Database DDBJ/EMBL/Genbank [online], Definition: LSU Ribosomal Protein L39E(RP139E) [Archaeoglobus Fulgidus DSM4304], 2004, EBI accession No. NP_070891.

Nelson, K.E. et al, 505 Ribosomal Protein L9, Database Uniprot, 2000, EBI accession No. Q9WZW7.1, Feb. 15, 2000.

Takami, H. et al, 50S Ribosomal Protein L9, Database Uniprot, 2004, EBI accession No. YP149330.1, Dec. 8, 2004.

Yuan Bi, et al., "Efficient High Level Expression of Peptide and Proteins As Fusion Proteins With the N—Terminal Domain of L9 Application to the Villin Headpiece Helical Subdomain," Protein Expression and Purification, 2005, vol. 47, pp. 234-240.

* cited by examiner mAU
80
60
40
20
0
mAU
0.0
5.0
10.0
15.0
20.0
25.0
30.0
35.0
40.0
ml
1
2
3
4
5
6
7
8
9
10
11
12
13
14
15
16
17
18
19
20
21
22
23
24
milliliter mAU
60.0
50.0
40.0
30.0
20.0
10.0
0.0
mAU
0
20
40
60
80
100
120
140
160
ml
milliliter
Waste Intensity
1294
1200
1100
1000
900
800
700
600
500
400
300
200
100
14810.41 Da
5000.0
1.0e4
1.5e4
2.0e4
2.5e4
3.0e4
3.5e4
4.0e4
m/z, Da Intensity
7.5e6
7.0e6
6.5e6
6.0e6
5.5e6
5.0e6
4.5e6
4.0e6
3.5e6
3.0e6
2.5e6
2.0e6
1.5e6
1.0e6
5.0e5
0.0
Peak 1
Peak 2
Peak 3
Peak 4
1.0
2.0
3.0
4.0
5.0
6.0
7.0
8.0
9.0
10.0
11.0
12.0
13.0
14.0
15.0
16.0
17.0
18.0
19.0
20.0
21.0
22.0
23.0
24.0
25.0
26.0
Time, min.

Intensity
516 500 480 460 440 420 400 380 360 340 320 300 280 260 240 220 200 180 160 140 120 100 80 60 40 20 0
750 800 850 900 950 1000 1050 1100 1150 1200 1250 1300 1350 1400
m/z, Da
[M+5H] 5+
[M+4H] 4+
[M+3H] 3+

Intensity
3.4e4
3.2e4
3.0e4
2.8e4
2.6e4
2.4e4
2.2e4
2.0e4
1.8e4
1.6e4
1.4e4
1.2e4
1.0e4
8000.0
6000.0
4000.0
2000.0
1.0e4
1.1e4
1.2e4
1.3e4
1.4e4
1.5e4
1.6e4
1.7e4
m/z, Da
12674,37 Da Intensity
7000
6500
6000
5500
5000
4500
4000
3500
3000
2500
2000
1500
1000
500
1.0e4
1.2e4
1.4e4
1.6e4
1.8e4
2.0e4
2.2e4
2.4e4
m/z, Da
16560,47 Da
12674,37 Da

SEQUENCE LISTING

```
<160> NUMBER OF SEQ ID NOS: 44

<210> SEQ ID NO 1
<211> LENGTH: 56
<212> TYPE: PRT
<213> ORGANISM: Bacillus stearothermophilus

<400> SEQUENCE: 1

Met Ser Lys Thr Ile Val Arg Lys Asn Glu Ser Ile Asp Asp Ala Leu
1               5                   10                  15

Arg Arg Phe Lys Arg Ala Val Ser Lys Thr Gly Thr Leu Gln Glu Val
            20                  25                  30

Arg Lys Arg Glu Phe Tyr Glu Lys Pro Ser Val Arg Arg Lys Lys Lys
        35                  40                  45

Ser Glu Ala Ala Arg Lys Arg Lys
    50                  55


<210> SEQ ID NO 2
<211> LENGTH: 50
<212> TYPE: PRT
<213> ORGANISM: Archaeoglobus fulgidus

<400> SEQUENCE: 2

Met Gly Lys Lys Thr Val Gly Val Lys Lys Arg Leu Ala Lys Ala Tyr
1               5                   10                  15

Lys Gln Asn Arg Arg Ala Pro Val Trp Ile Thr Val Lys Thr Lys Arg
            20                  25                  30

Ser Val Phe Gly Ser Pro Lys Arg Arg His Trp Arg Arg Ser Lys Leu
        35                  40                  45

Lys Val
    50


<210> SEQ ID NO 3
<211> LENGTH: 44
<212> TYPE: PRT
```

<213> ORGANISM: Thermotoga maritima

<400> SEQUENCE: 3

```
Met Lys Arg Thr Tyr Gln Pro Ser Arg Arg Lys Arg Lys Arg Thr His
1               5                   10                  15

Gly Phe Leu Ala Arg Lys Arg Thr Pro Gly Gly Arg Arg Val Leu Lys
            20                  25                  30

Asn Arg Arg Arg Lys Gly Arg Trp Arg Leu Thr Val
        35                  40
```

<210> SEQ ID NO 4
<211> LENGTH: 27
<212> TYPE: PRT
<213> ORGANISM: Thermus thermophilus

<400> SEQUENCE: 4

```
Met Gly Lys Gly Asp Arg Arg Thr Arg Arg Gly Lys Ile Trp Arg Gly
1               5                   10                  15

Thr Tyr Gly Lys Tyr Arg Pro Arg Lys Lys Lys
            20                  25
```

<210> SEQ ID NO 5
<211> LENGTH: 67
<212> TYPE: PRT
<213> ORGANISM: Thermotoga maritima

<400> SEQUENCE: 5

```
Met Ala Lys Val Lys Met Lys Thr Asn Arg Ser Ala Ala Lys Arg Phe
1               5                   10                  15

Lys Val Thr Ala Lys Gly Lys Ile Lys Arg Trp Lys Ser Gly Gly Ala
            20                  25                  30

His Tyr Asn Thr Lys Lys Ser Ser Lys Arg Lys Arg His Leu Arg Lys
        35                  40                  45

His Thr Tyr Val Lys Asp Asn Met Leu Lys His Val Lys Ala Leu Leu
    50                  55                  60

Lys Glu Phe
65
```

<210> SEQ ID NO 6
<211> LENGTH: 10
<212> TYPE: PRT
<213> ORGANISM: Artificial
<220> FEATURE:
<223> OTHER INFORMATION: Synthetic

<400> SEQUENCE: 6

```
Arg Arg Gly Gly Ser Asp Asp Asp Asp Lys
1               5                   10
```

<210> SEQ ID NO 7
<211> LENGTH: 8
<212> TYPE: PRT
<213> ORGANISM: Artificial
<220> FEATURE:
<223> OTHER INFORMATION: Synthetic

<400> SEQUENCE: 7

```
Ser Ser Ser Asp Asp Asp Asp Lys
1               5
```

<210> SEQ ID NO 8
<211> LENGTH: 15
<212> TYPE: PRT

<213> ORGANISM: Artificial
<220> FEATURE:
<223> OTHER INFORMATION: Synthetic

<400> SEQUENCE: 8

Ser Ser Ser Ser Thr Ser Ser Ser Ser Thr Asp Asp Asp Asp Lys
1 5 10 15

<210> SEQ ID NO 9
<211> LENGTH: 15
<212> TYPE: PRT
<213> ORGANISM: Artificial
<220> FEATURE:
<223> OTHER INFORMATION: Synthetic

<400> SEQUENCE: 9

Ser Ser Ser Ser Thr Leu Ala Ala Pro Phe Asp Asp Asp Asp Lys
1 5 10 15

<210> SEQ ID NO 10
<211> LENGTH: 5
<212> TYPE: PRT
<213> ORGANISM: Homo sapiens

<400> SEQUENCE: 10

Asp Asp Asp Asp Lys
1 5

<210> SEQ ID NO 11
<211> LENGTH: 4
<212> TYPE: PRT
<213> ORGANISM: Artificial
<220> FEATURE:
<223> OTHER INFORMATION: Synthetic

<400> SEQUENCE: 11

Ile Glu Gly Arg
1

<210> SEQ ID NO 12
<211> LENGTH: 5
<212> TYPE: PRT
<213> ORGANISM: Artificial
<220> FEATURE:
<223> OTHER INFORMATION: Synthetic

<400> SEQUENCE: 12

Leu Val Pro Arg Gly
1 5

<210> SEQ ID NO 13
<211> LENGTH: 6
<212> TYPE: PRT
<213> ORGANISM: Artificial
<220> FEATURE:
<223> OTHER INFORMATION: Synthetic

<400> SEQUENCE: 13

Leu Val Pro Arg Gly Ser
1 5

<210> SEQ ID NO 14
<211> LENGTH: 7
<212> TYPE: PRT
<213> ORGANISM: Artificial
<220> FEATURE:
<223> OTHER INFORMATION: Synthetic
<220> FEATURE:

```
<221> NAME/KEY: peptide
<222> LOCATION: (7)..(7)
<220> FEATURE:
<221> NAME/KEY: peptide
<222> LOCATION: (7)..(7)
<223> OTHER INFORMATION: X can be Gly or Ser

<400> SEQUENCE: 14

Glu Asn Leu Tyr Phe Gln Xaa
1               5


<210> SEQ ID NO 15
<211> LENGTH: 11
<212> TYPE: PRT
<213> ORGANISM: Artificial
<220> FEATURE:
<223> OTHER INFORMATION: Synthetic

<400> SEQUENCE: 15

Ala Leu Ala Ala Pro Phe Asp Asp Asp Asp Lys
1               5                   10


<210> SEQ ID NO 16
<211> LENGTH: 9
<212> TYPE: PRT
<213> ORGANISM: Artificial
<220> FEATURE:
<223> OTHER INFORMATION: Synthetic

<400> SEQUENCE: 16

Ser Ser Ser Ser Asp Asp Asp Asp Lys
1               5


<210> SEQ ID NO 17
<211> LENGTH: 11
<212> TYPE: PRT
<213> ORGANISM: Artificial
<220> FEATURE:
<223> OTHER INFORMATION: Synthetic

<400> SEQUENCE: 17

Ser Ser Ser Ser Ser Leu Glu Val Leu Phe Gln
1               5                   10


<210> SEQ ID NO 18
<211> LENGTH: 14
<212> TYPE: PRT
<213> ORGANISM: Artificial
<220> FEATURE:
<223> OTHER INFORMATION: Synthetic

<400> SEQUENCE: 18

Ser Ser Ser Ala Leu Ala Ala Pro Ala Asp Asp Asp Asp Lys
1               5                   10


<210> SEQ ID NO 19
<211> LENGTH: 10
<212> TYPE: PRT
<213> ORGANISM: Artificial
<220> FEATURE:
<223> OTHER INFORMATION: Synthetic

<400> SEQUENCE: 19

Ser Ser Ser Ser Glu Asn Leu Tyr Phe Gln
1               5                   10


<210> SEQ ID NO 20
<211> LENGTH: 233
```

<212> TYPE: PRT
<213> ORGANISM: Thermotoga maritima

<400> SEQUENCE: 20

```
Met Pro Lys His Ser Lys Arg Tyr Leu Glu Ala Arg Lys Leu Val Asp
1               5                   10                  15

Arg Thr Lys Tyr Tyr Asp Leu Asp Glu Ala Ile Glu Leu Val Lys Lys
            20                  25                  30

Thr Ala Thr Ala Lys Phe Asp Glu Thr Ile Glu Leu His Ile Gln Thr
        35                  40                  45

Gly Ile Asp Tyr Arg Lys Pro Glu Gln His Ile Arg Gly Thr Ile Val
    50                  55                  60

Leu Pro His Gly Thr Gly Lys Glu Val Lys Val Leu Val Phe Ala Lys
65                  70                  75                  80

Gly Glu Lys Ala Lys Glu Ala Leu Glu Ala Gly Ala Asp Tyr Val Gly
                85                  90                  95

Ala Glu Asp Leu Val Glu Lys Ile Glu Lys Glu Gly Phe Leu Asp Phe
            100                 105                 110

Asp Val Ala Ile Ala Thr Pro Asp Met Met Arg Ile Ile Gly Arg Leu
        115                 120                 125

Gly Lys Ile Leu Gly Pro Arg Gly Leu Met Pro Ser Pro Lys Ser Gly
    130                 135                 140

Thr Val Thr Gln Glu Val Ala Glu Ala Val Lys Glu Phe Lys Lys Gly
145                 150                 155                 160

Arg Ile Glu Val Arg Thr Asp Lys Thr Gly Asn Ile His Ile Pro Val
                165                 170                 175

Gly Lys Arg Ser Phe Asp Asn Glu Lys Leu Lys Glu Asn Ile Ile Ala
            180                 185                 190

Ala Ile Lys Gln Ile Met Gln Met Lys Pro Ala Gly Val Lys Gly Gln
        195                 200                 205

Phe Ile Lys Lys Val Val Leu Ala Ser Thr Met Gly Pro Gly Ile Lys
    210                 215                 220

Leu Asn Leu Gln Ser Leu Leu Lys Glu
225                 230
```

<210> SEQ ID NO 21
<211> LENGTH: 235
<212> TYPE: PRT
<213> ORGANISM: Thermotoga maritima

<400> SEQUENCE: 21

```
Met Ala Gln Val Asp Leu Leu Asn Val Lys Gly Glu Lys Val Gly Thr
1               5                   10                  15

Leu Glu Ile Ser Asp Phe Val Phe Asn Ile Asp Pro Asn Tyr Asp Val
            20                  25                  30

Met Trp Arg Tyr Val Asp Met Gln Leu Ser Asn Arg Arg Ala Gly Thr
        35                  40                  45

Ala Ser Thr Lys Thr Arg Gly Glu Val Ser Gly Gly Gly Arg Lys Pro
    50                  55                  60

Trp Pro Gln Lys His Thr Gly Arg Ala Arg His Gly Ser Ile Arg Ser
65                  70                  75                  80

Pro Ile Trp Arg His Gly Gly Val Val His Gly Pro Lys Pro Arg Asp
                85                  90                  95

Trp Ser Lys Lys Leu Asn Lys Lys Met Lys Lys Leu Ala Leu Arg Ser
            100                 105                 110

Ala Leu Ser Val Lys Tyr Arg Glu Asn Lys Leu Leu Val Leu Asp Asp
```

```
        115                 120                 125

Leu Lys Leu Glu Arg Pro Lys Thr Lys Ser Leu Lys Glu Ile Leu Gln
    130                 135                 140

Asn Leu Gln Leu Ser Asp Lys Lys Thr Leu Ile Val Leu Pro Trp Lys
145                 150                 155                 160

Glu Glu Gly Tyr Met Asn Val Lys Leu Ser Gly Arg Asn Leu Pro Asp
                165                 170                 175

Val Lys Val Ile Ile Ala Asp Asn Pro Asn Asn Ser Lys Asn Gly Glu
            180                 185                 190

Lys Ala Val Arg Ile Asp Gly Leu Asn Val Phe Asp Met Leu Lys Tyr
        195                 200                 205

Asp Tyr Leu Val Leu Thr Arg Asp Met Val Ser Lys Ile Glu Glu Val
    210                 215                 220

Leu Gly Asn Glu Ala Gly Lys Ala Leu Thr Ala
225                 230                 235


<210> SEQ ID NO 22
<211> LENGTH: 184
<212> TYPE: PRT
<213> ORGANISM: Thermotoga maritima

<400> SEQUENCE: 22

Met Arg Tyr Glu Tyr Val Pro Leu Lys Asp Gln Tyr Glu Lys Glu Ile
1               5                   10                  15

Val Pro Ala Leu Met Lys Glu Phe Asn Tyr Lys Asn Ile His Gln Val
            20                  25                  30

Pro Lys Leu Val Lys Ile Val Ile Asn Met Gly Ile Gly Glu Gly Ser
        35                  40                  45

Arg Asn Tyr Asp Leu Ile Glu Arg His Ala Asn Glu Leu Ala Lys Ile
    50                  55                  60

Thr Gly Gln Lys Pro Ile Val Thr Arg Ala Arg Lys Ser Ile Ser Asn
65                  70                  75                  80

Phe Lys Ile Arg Lys Gly Met Pro Ile Gly Leu Lys Val Thr Leu Arg
                85                  90                  95

Gly Ala Arg Met Tyr Asn Phe Leu Tyr Lys Leu Ile Asn Ile Val Leu
            100                 105                 110

Pro Lys Val Arg Asp Phe Arg Gly Leu Asp Pro Asn Ser Phe Asp Gly
        115                 120                 125

Arg Gly Asn Tyr Ser Phe Gly Leu Ser Glu Gln Leu Val Phe Pro Glu
    130                 135                 140

Leu Asn Pro Asp Glu Val Arg Arg Ile Gln Gly Met Asp Ile Thr Ile
145                 150                 155                 160

Val Thr Thr Ala Lys Thr Asp Gln Glu Ala Arg Arg Leu Leu Glu Leu
                165                 170                 175

Phe Gly Met Pro Phe Lys Arg Gly
            180


<210> SEQ ID NO 23
<211> LENGTH: 184
<212> TYPE: PRT
<213> ORGANISM: Thermotoga maritima

<400> SEQUENCE: 23

Met Ser Arg Leu Ala Lys Lys Pro Ile Val Leu Pro Gln Gly Val Thr
1               5                   10                  15

Val Glu Ile Lys Asp Asn Val Val Lys Val Lys Gly Pro Lys Gly Glu
            20                  25                  30
```

```
Leu Ser Gln Glu Phe Leu Pro Tyr Val Lys Ile Glu Val Glu Gly Asn
        35                  40                  45

Glu Val Trp Val Arg Pro Asn Glu Glu Gln Ile Ile Arg Lys Ser Asp
    50                  55                  60

Trp Arg Lys Val Lys Met Phe Gln Gly Thr Tyr Trp Ser Leu Ile Arg
65                  70                  75                  80

Asn Met Val Val Gly Val Thr Glu Gly Tyr Lys Lys Glu Leu Glu Ile
                85                  90                  95

Val Gly Ile Gly Tyr Arg Ala Gln Leu Gln Gly Asn Thr Leu Val Met
            100                 105                 110

Asn Leu Gly Tyr Ala His Pro Val Val Tyr Glu Ile Pro Ser Asp Val
        115                 120                 125

Lys Ile Glu Val Pro Ala Pro Asn Arg Ile Ile Val Ser Gly Ile Asp
    130                 135                 140

Lys Gln Arg Val Gly Gln Val Ala Ala Glu Ile Arg Ala Phe Arg Pro
145                 150                 155                 160

Pro Asn Val Tyr Thr Gly Lys Gly Ile Arg Tyr Val Gly Glu Val Val
                165                 170                 175

Arg Gln Lys Glu Gly Lys Lys Ala
            180


<210> SEQ ID NO 24
<211> LENGTH: 149
<212> TYPE: PRT
<213> ORGANISM: Thermotoga maritima

<400> SEQUENCE: 24

Met Lys Val Ile Leu Leu Arg Asp Val Pro Lys Ile Gly Lys Lys Gly
1               5                   10                  15

Glu Ile Lys Glu Val Ser Asp Gly Tyr Ala Arg Asn Tyr Leu Ile Pro
            20                  25                  30

Arg Gly Phe Ala Lys Glu Tyr Thr Glu Gly Leu Glu Arg Ala Ile Lys
        35                  40                  45

His Glu Lys Glu Ile Glu Lys Arg Lys Lys Glu Arg Glu Arg Glu Glu
    50                  55                  60

Ser Glu Lys Ile Leu Lys Glu Leu Lys Lys Arg Thr His Val Val Lys
65                  70                  75                  80

Val Lys Ala Gly Glu Gly Gly Lys Ile Phe Gly Ala Val Thr Ala Ala
                85                  90                  95

Thr Val Ala Glu Glu Ile Ser Lys Thr Thr Gly Leu Lys Leu Asp Lys
            100                 105                 110

Arg Trp Phe Lys Leu Asp Lys Pro Ile Lys Glu Leu Gly Glu Tyr Ser
        115                 120                 125

Leu Glu Val Ser Leu Pro Gly Gly Val Lys Asp Thr Ile Lys Ile Arg
    130                 135                 140

Val Glu Arg Glu Glu
145


<210> SEQ ID NO 25
<211> LENGTH: 179
<212> TYPE: PRT
<213> ORGANISM: Thermotoga maritima

<400> SEQUENCE: 25

Met Leu Thr Arg Gln Gln Lys Glu Leu Ile Val Lys Glu Met Ser Glu
1               5                   10                  15
```

```
Ile Phe Lys Lys Thr Ser Leu Ile Leu Phe Ala Asp Phe Leu Gly Phe
            20                  25                  30

Thr Val Ala Asp Leu Thr Glu Leu Arg Ser Arg Leu Arg Glu Lys Tyr
        35                  40                  45

Gly Asp Gly Ala Arg Phe Arg Val Val Lys Asn Thr Leu Leu Asn Leu
    50                  55                  60

Ala Leu Lys Asn Ala Glu Tyr Glu Gly Tyr Glu Glu Phe Leu Lys Gly
65                  70                  75                  80

Pro Thr Ala Val Leu Tyr Val Thr Glu Gly Asp Pro Val Glu Ala Val
                85                  90                  95

Lys Ile Ile Tyr Asn Phe Tyr Lys Asp Lys Lys Ala Asp Leu Ser Arg
            100                 105                 110

Leu Lys Gly Gly Phe Leu Glu Gly Lys Lys Phe Thr Ala Glu Glu Val
        115                 120                 125

Glu Asn Ile Ala Lys Leu Pro Ser Lys Glu Glu Leu Tyr Ala Met Leu
    130                 135                 140

Val Gly Arg Val Lys Ala Pro Ile Thr Gly Leu Val Phe Ala Leu Ser
145                 150                 155                 160

Gly Ile Leu Arg Asn Leu Val Tyr Val Leu Asn Ala Ile Lys Glu Lys
                165                 170                 175

Lys Ser Glu


<210> SEQ ID NO 26
<211> LENGTH: 149
<212> TYPE: PRT
<213> ORGANISM: Thermotoga maritima

<400> SEQUENCE: 26

Met Ala Arg Tyr Phe Pro Val Gln Lys Thr Thr Met Ile Lys Pro Glu
1               5                   10                  15

Glu Val Glu Arg Lys Trp Tyr Val Val Asp Ala Ser Gly Lys Val Leu
            20                  25                  30

Gly Arg Leu Ala Thr Arg Ile Ala Lys Ile Leu Met Gly Lys His Lys
        35                  40                  45

Pro Asn Tyr Thr Pro His Val Asp Thr Gly Asp Tyr Val Ile Val Val
    50                  55                  60

Asn Ala Asp Lys Val Val Leu Thr Gly Lys Lys Leu Asp Gln Lys Val
65                  70                  75                  80

Tyr Tyr Trp His Ser Gly Tyr Pro Gly Gly Leu Lys Ser Leu Thr Ala
                85                  90                  95

Arg Gln Met Leu Glu Lys His Pro Glu Arg Leu Ile Trp Leu Ala Val
            100                 105                 110

Lys Arg Met Leu Pro Lys Asn Arg Lys Gly Arg Lys Met Leu Lys Arg
        115                 120                 125

Leu Lys Val Tyr Ala Ser Pro Glu His Pro His Gln Ala Gln Lys Pro
    130                 135                 140

Glu Pro Ile Glu Leu
145


<210> SEQ ID NO 27
<211> LENGTH: 147
<212> TYPE: PRT
<213> ORGANISM: Thermotoga maritima

<400> SEQUENCE: 27

Met Arg Leu Glu Asp Leu Arg Pro Thr Pro Gly Ala Met Lys Lys Arg
1               5                   10                  15
```

```
Lys Arg Val Gly Arg Gly Pro Gly Ser Gly His Gly Lys Thr Ser Gly
            20                  25                  30

Arg Gly His Lys Gly Gln Lys Ala Arg Gly Ser Gly Lys Val His Ile
        35                  40                  45

Trp Phe Glu Gly Gly Gln Thr Pro Leu Gln Arg Arg Leu Pro Lys Arg
    50                  55                  60

Gly Phe Lys Asn Ile Asn Lys Lys Val Tyr Ala Val Val Asn Val Lys
65                  70                  75                  80

Val Leu Glu Glu Arg Phe Glu Ala Asn Glu Glu Val Thr Pro Glu Lys
                85                  90                  95

Leu Ile Glu Arg Lys Ile Ile Lys Asp Leu Lys Asp Gly Val Lys Ile
            100                 105                 110

Leu Gly Asp Gly Glu Leu Thr Lys Pro Leu Val Val Lys Ala His Ala
        115                 120                 125

Phe Ser Lys Ser Ala Val Glu Lys Ile Glu Ser Ala Gly Gly Lys Ala
    130                 135                 140

Glu Val Ile
145


<210> SEQ ID NO 28
<211> LENGTH: 131
<212> TYPE: PRT
<213> ORGANISM: Thermotoga maritima

<400> SEQUENCE: 28

Met Arg His Arg Val Lys Arg His Lys Leu Gly Arg Tyr Gly Ser His
1               5                   10                  15

Arg Lys Ser Leu Leu Arg Asn Leu Ser Arg Glu Ile Val Glu His Gly
            20                  25                  30

Ser Ile Val Thr Thr Thr Ala Lys Ala Lys Ala Leu Lys Thr Phe Met
        35                  40                  45

Asp Lys Leu Val Ser Lys Ala Ile Glu Ala Ala Thr Thr Asp Asp Arg
    50                  55                  60

Ala Arg Ser Val His Leu Arg Arg Gln Ile Asn Ala Val Leu Gly Asp
65                  70                  75                  80

Arg Arg Leu Thr Asn Lys Leu Val Asp Glu Ile Ala Lys Asn Tyr Val
                85                  90                  95

Gly Arg Arg Gly Gly Tyr Val Arg Val Leu Arg Ile Gly Phe Arg Arg
            100                 105                 110

Gly Asp Ala Ala Glu Met Ser Leu Val Gln Leu Val Glu Ala Ser Ser
        115                 120                 125

Gln Glu Gly
    130


<210> SEQ ID NO 29
<211> LENGTH: 115
<212> TYPE: PRT
<213> ORGANISM: Thermotoga maritima

<400> SEQUENCE: 29

Met Asp His Leu Val Lys Ile Ile Glu Lys Lys Tyr Glu Lys Lys Glu
1               5                   10                  15

Ile Pro Asp Phe Arg Pro Gly Asp Thr Val Arg Val His Val Lys Val
            20                  25                  30

Ile Glu Gly Asp Arg Glu Arg Thr Gln Val Phe Glu Gly Ile Val Ile
        35                  40                  45
```

```
Ala Lys Arg Gly Ser Gly Ile Asn Lys Thr Phe Thr Val Arg Arg Ile
    50                  55                  60

Gly Ser His Gly Val Gly Val Glu Arg Ile Phe Pro Val His Ser Pro
65                  70                  75                  80

Val Val Glu Lys Ile Glu Val Val Arg Lys Gly Lys Val Arg Arg Ala
                85                  90                  95

Lys Leu Tyr Tyr Leu Arg Asn Val Arg Gly Lys Ile Arg Ile Lys Glu
            100                 105                 110

Arg Arg Asp
        115


<210> SEQ ID NO 30
<211> LENGTH: 118
<212> TYPE: PRT
<213> ORGANISM: Thermotoga maritima

<400> SEQUENCE: 30

Met Arg Val Lys Arg Ala Val His Ala Lys Lys Lys Arg Lys Lys Tyr
1               5                   10                  15

Leu Lys Ala Ala Lys Gly Tyr Arg Gly Ala Leu Ser Arg Arg Tyr Lys
            20                  25                  30

Leu Ala Lys Gln Met Tyr Val Arg Ser Lys Trp Tyr Ser Tyr Val Gly
        35                  40                  45

Arg Lys Gln Lys Lys Arg Asp Met Arg Lys Leu Trp Ile Thr Arg Ile
    50                  55                  60

Asn Ile Ala Ala Arg Asn Glu Gly Leu Lys Tyr Ser Glu Leu Ile His
65                  70                  75                  80

Gly Leu Lys Leu Ala Gly Val Ser Ile Asn Arg Lys Met Leu Ser Glu
                85                  90                  95

Leu Ala Val Asn Asp Pro Glu Ala Phe Lys Glu Tyr Val Lys Ile Ala
            100                 105                 110

Lys Glu Ala Leu Ala Ser
        115


<210> SEQ ID NO 31
<211> LENGTH: 105
<212> TYPE: PRT
<213> ORGANISM: Thermotoga maritima

<400> SEQUENCE: 31

Met Leu Tyr Ala Ile Val Glu Thr Ala Gly Arg Gln Tyr Arg Val Glu
1               5                   10                  15

Glu Gly Lys Ile Leu Tyr Thr Glu Lys Gln Lys Asp Tyr Ser Pro Gly
            20                  25                  30

Asp Glu Ile Val Phe Asp Arg Val Val Phe Val Arg Lys Asp Gly Glu
        35                  40                  45

Val Leu Val Gly Lys Pro Tyr Val Glu Gly Ala Lys Val Val Gly Lys
    50                  55                  60

Val Leu Glu His Ala Lys Ala Arg Lys Val Lys Thr Val Lys Tyr Arg
65                  70                  75                  80

Pro Arg Lys Asn Ser Lys Val Glu Lys Gly His Arg Gln Trp Tyr Thr
                85                  90                  95

Ala Ile Lys Ile Glu Lys Ile Glu Leu
            100                 105


<210> SEQ ID NO 32
<211> LENGTH: 100
<212> TYPE: PRT
```

```
<213> ORGANISM: Thermotoga maritima

<400> SEQUENCE: 32

Met Lys Gln Glu Lys Leu Ser Leu His Asp Val Leu Ile Arg Pro Ile
1               5                   10                  15

Ile Thr Glu Lys Ala Leu Ile Leu Arg Glu Gln Arg Lys Tyr Val Phe
            20                  25                  30

Glu Val Asn Pro Leu Ala Asn Lys Asn Leu Val Lys Glu Ala Val Glu
        35                  40                  45

Lys Leu Phe Asn Val Lys Val Glu Lys Val Asn Ile Leu Asn Met Lys
    50                  55                  60

Pro Lys Pro Lys Arg Arg Gly Ile Phe Glu Gly Lys Thr Arg Ser Trp
65                  70                  75                  80

Lys Lys Ala Val Val Thr Leu Lys Glu Gly Tyr Thr Ile Lys Glu Leu
                85                  90                  95

Glu Gly Glu His
            100


<210> SEQ ID NO 33
<211> LENGTH: 83
<212> TYPE: PRT
<213> ORGANISM: Thermotoga maritima

<400> SEQUENCE: 33

Met Ala His Lys Lys Ser Gly Gly Val Ala Lys Asn Gly Arg Asp Ser
1               5                   10                  15

Leu Pro Lys Tyr Leu Gly Val Lys Val Gly Asp Gly Gln Ile Val Lys
            20                  25                  30

Ala Gly Asn Ile Leu Val Arg Gln Arg Gly Thr Arg Phe Tyr Pro Gly
        35                  40                  45

Lys Asn Val Gly Met Gly Arg Asp Phe Thr Leu Phe Ala Leu Lys Asp
    50                  55                  60

Gly Arg Val Lys Phe Glu Thr Lys Asn Asn Lys Lys Tyr Val Ser Val
65                  70                  75                  80

Tyr Glu Glu


<210> SEQ ID NO 34
<211> LENGTH: 66
<212> TYPE: PRT
<213> ORGANISM: Thermotoga maritima

<400> SEQUENCE: 34

Met Lys Ala Ser Glu Leu Arg Asn Tyr Thr Asp Glu Glu Leu Lys Asn
1               5                   10                  15

Leu Leu Glu Glu Lys Lys Arg Gln Leu Met Glu Leu Arg Phe Gln Leu
            20                  25                  30

Ala Met Gly Gln Leu Lys Asn Thr Ser Leu Ile Lys Leu Thr Lys Arg
        35                  40                  45

Asp Ile Ala Arg Ile Lys Thr Ile Leu Arg Glu Arg Glu Leu Gly Ile
    50                  55                  60

Arg Arg
65


<210> SEQ ID NO 35
<211> LENGTH: 67
<212> TYPE: PRT
<213> ORGANISM: Thermotoga maritima

<400> SEQUENCE: 35
```

```
Met Pro Lys Lys Leu Lys Ile Lys Leu Val Lys Ser Pro Ile Gly Tyr
1               5                   10                  15

Ser Trp Asp Gln Lys Asp Thr Val Lys Arg Leu Gly Leu Lys Lys Leu
            20                  25                  30

Asn Gln Val Val Ile Lys Asp Asp Leu Pro Gln Ile Arg Gly Met Ile
        35                  40                  45

Arg Lys Val Lys His Leu Val Glu Val Glu Glu Ile Glu Glu Gly Gly
    50                  55                  60

Ser Asn Ala
65


<210> SEQ ID NO 36
<211> LENGTH: 44
<212> TYPE: PRT
<213> ORGANISM: Thermotoga maritima

<400> SEQUENCE: 36

Met Lys Arg Thr Tyr Gln Pro Ser Arg Arg Lys Arg Lys Arg Thr His
1               5                   10                  15

Gly Phe Leu Ala Arg Lys Arg Thr Pro Gly Gly Arg Arg Val Leu Lys
            20                  25                  30

Asn Arg Arg Arg Lys Gly Arg Trp Arg Leu Thr Val
        35                  40


<210> SEQ ID NO 37
<211> LENGTH: 65
<212> TYPE: PRT
<213> ORGANISM: Thermotoga maritima

<400> SEQUENCE: 37

Met Pro Lys Val Lys Thr Asn Arg Ser Ala Ala Lys Arg Phe Arg Ile
1               5                   10                  15

Thr Lys Asn Gly Lys Ile Met Arg Asn His Ala Tyr Arg Ser His Lys
            20                  25                  30

Thr Gly Lys Lys Arg Arg Asn Ala Leu Arg Ala Leu Arg Lys Lys Asp
        35                  40                  45

Val Val Ser Ser Ala Asp Lys Asn Arg Val Leu Arg Leu Leu Gly Lys
    50                  55                  60

Lys
65


<210> SEQ ID NO 38
<211> LENGTH: 209
<212> TYPE: PRT
<213> ORGANISM: Thermotoga maritima

<400> SEQUENCE: 38

Met Gly Gln Lys Val His Pro Arg Gly Phe Arg Leu Gly Leu Ser Ala
1               5                   10                  15

Asp Trp Gln Ala Lys Trp Phe Asn Glu Lys Asn Tyr Lys Glu Trp Leu
            20                  25                  30

Leu Glu Asp Glu Glu Ile Arg Lys Ile Ile Lys Asn Lys Tyr Tyr His
        35                  40                  45

Ala Gly Ile Ser Glu Ile Tyr Val Glu Arg Pro Asp Ala Glu Arg Ile
    50                  55                  60

Asn Ile Thr Val Lys Thr Ala Arg Pro Gly Ile Ile Ile Gly Arg Lys
65                  70                  75                  80

Gly Ser Glu Ile Thr Ser Leu Arg Glu Glu Leu Glu Arg Lys Phe Asn
```

```
                85                  90                  95

Arg Arg Val Val Ile Asn Ile Glu Glu Ile Lys Thr Pro Glu Leu Asp
            100                 105                 110

Ala Gln Leu Val Ala Glu Ser Ile Ala Ser Arg Ile Glu Lys Arg Ala
        115                 120                 125

Ser Tyr Lys Val Ala Met Lys Arg Ala Ile Met Asn Ala Met Arg Lys
    130                 135                 140

Gly Ala Gln Gly Ile Lys Val Met Val Ala Gly Arg Leu Gly Gly Ala
145                 150                 155                 160

Glu Ile Ala Arg Arg Glu Trp Tyr Leu Arg Gly Arg Leu Pro Leu Gln
                165                 170                 175

Lys Ile Lys Ala Ile Ile Asp Tyr Gly Thr Ala Thr Ala Trp Thr Lys
            180                 185                 190

Tyr Gly Thr Ile Gly Ile Lys Val Trp Ile Tyr Lys Gly Asp Ala Asp
        195                 200                 205

Ile


<210> SEQ ID NO 39
<211> LENGTH: 178
<212> TYPE: PRT
<213> ORGANISM: Thermotoga maritima

<400> SEQUENCE: 39

Met Glu Thr Gln Gly Val Met Lys Glu Ile Gln Tyr Glu Glu Phe Glu
1               5                   10                  15

Glu Lys Ile Ile Glu Ile Arg Arg Thr Ser Lys Val Thr Lys Gly Gly
            20                  25                  30

Lys Asn Leu Ser Phe Arg Val Val Ala Ile Val Gly Asn Lys Asn Gly
        35                  40                  45

Lys Val Gly Leu Gly Ile Gly Lys Ala Arg Glu Val Pro Glu Ala Ile
    50                  55                  60

Arg Lys Ala Ile Ser Ala Ala Lys Arg Asn Ile Val Glu Val Pro Val
65                  70                  75                  80

Ile Asn Gly Thr Ile Pro His Glu Val Ile Gly Arg Gln Asp Ala Ser
                85                  90                  95

Lys Val Leu Leu Lys Pro Ala Ala Pro Gly Thr Gly Ile Ile Ala Gly
            100                 105                 110

Gly Thr Val Arg Ala Val Val Glu Leu Ala Gly Ile Gln Asn Ile Leu
        115                 120                 125

Thr Lys Ser Leu Gly Ser Thr Asn Pro Leu Asn Leu Ala Leu Ala Thr
    130                 135                 140

Met Asn Gly Leu Lys Asn Leu Leu Asp Pro Arg Lys Val Ala Lys Leu
145                 150                 155                 160

Arg Asp Ile Ser Val Glu Glu Val Phe Lys Gly Val Arg Arg Glu Asn
                165                 170                 175

Asn Ala


<210> SEQ ID NO 40
<211> LENGTH: 90
<212> TYPE: PRT
<213> ORGANISM: Thermotoga maritima

<400> SEQUENCE: 40

Met Val Ser Leu Asp Pro Glu Lys Lys Asn Glu Ile Ile Lys Glu Phe
1               5                   10                  15

Gln Ile His Glu Asn Asp Thr Gly Ser Val Glu Val Gln Ile Ala Leu
```

```
            20                  25                  30

Leu Thr Ala Arg Ile Lys His Leu Thr Glu His Leu Arg Lys His Pro
        35                  40                  45

Lys Asp Phe His Ser Arg Arg Gly Leu Met Lys Met Ile Gly Arg Arg
    50                  55                  60

Arg Lys Met Leu Lys Tyr Leu Arg His Lys Lys Pro Glu Val Tyr Arg
65                  70                  75                  80

Glu Leu Ile Ala Lys Leu Gly Ile Arg Lys
                85                  90


<210> SEQ ID NO 41
<211> LENGTH: 95
<212> TYPE: PRT
<213> ORGANISM: Thermotoga maritima

<400> SEQUENCE: 41

Met Gly Arg Ser Arg Lys Lys Gly Pro Tyr Val Asp Arg Lys Leu Leu
1               5                   10                  15

Glu Lys Ile Arg Lys Leu Asn Glu Thr Gly Glu Lys Lys Val Ile Lys
            20                  25                  30

Thr Trp Ser Arg Ala Ser Met Ile Ile Pro Glu Met Val Gly His Thr
        35                  40                  45

Ile Ala Val Tyr Asn Gly Met Lys His Ile Pro Val Tyr Ile Thr Glu
    50                  55                  60

Asn Met Ile Gly His Arg Leu Gly Glu Phe Ala Pro Thr Arg Arg Phe
65                  70                  75                  80

Gly Gly His Ala Asp Lys Lys Ala Lys Lys Gly Glu Leu Lys Lys
                85                  90                  95


<210> SEQ ID NO 42
<211> LENGTH: 96
<212> TYPE: PRT
<213> ORGANISM: Thermotoga maritima

<400> SEQUENCE: 42

Met Pro Asn Ile Lys Ser Ala Lys Lys Arg Val Arg Val Ser Glu Lys
1               5                   10                  15

Arg Arg Leu Arg Asn Lys Ala Tyr Lys Thr Phe Phe Lys Asn Arg Ile
            20                  25                  30

Lys Glu Val Leu Lys Ala Ile Glu Asn Lys Glu Pro Lys Glu Val Val
        35                  40                  45

Leu Glu Leu Thr Arg Lys Ala Gln Ala Ala Ile Asp Lys Ala Val Ser
    50                  55                  60

Lys Gly Val Ile His Lys Asn Gln Gly Ala Arg Arg Lys Ala Arg Leu
65                  70                  75                  80

Phe Glu Lys Val Asn Glu Tyr Leu Arg Thr Leu Glu Thr Thr Gln Glu
                85                  90                  95


<210> SEQ ID NO 43
<211> LENGTH: 43
<212> TYPE: PRT
<213> ORGANISM: Artificial
<220> FEATURE:
<223> OTHER INFORMATION: Synthetic

<400> SEQUENCE: 43

Gly Ser Leu Asp Glu Ser Phe Tyr Asp Trp Phe Glu Arg Gln Leu Gly
1               5                   10                  15

Gly Gly Ser Gly Gly Ser Ser Leu Glu Glu Glu Trp Ala Gln Ile Gln
```

-continued

```
            20                  25                  30

Cys Glu Val Trp Gly Arg Gly Cys Pro Ser Tyr
        35                  40


<210> SEQ ID NO 44
<211> LENGTH: 37
<212> TYPE: PRT
<213> ORGANISM: Homo sapiens

<400> SEQUENCE: 44

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35
```

BASIC PROTEIN PURIFICATION TAGS FROM THERMOPHILIC BACTERIA

CROSS-REFERENCE TO RELATED APPLICATIONS

This application is a 35 U.S.C. §371 national stage application of International Patent Application PCT/EP2006/061493 (published as WO 2006/108826), filed Apr. 10, 2006, which claimed priority of Danish Patent Application PA 2005 00549, filed Apr. 15, 2005; this application further claims priority under 35 U.S.C. §119 of U.S. Provisional Application 60/675,054, filed Apr. 26, 2005.

FIELD OF THE INVENTION

The present invention is related to a method of purifying recombinant proteins by use of a certain group of positively charged tags derived from thermophilic bacteria.

BACKGROUND OF THE INVENTION

Purification of native or non-native recombinant proteins from bacterial or eukaryotic cells often requires several steps. Methods to reduce the number of steps in a purification of a target protein are advantageous for cheap and efficient production of recombinant proteins. Purification of target proteins fused to small highly basic domains is disclosed by Graslund et al., Protein Eng. 2000, 13(10):703-709, Graslund et al., J Chromatogr A. 2002, 942(1-2):157-166 and Graslund et al., Journal of Biotechnology, 2002, 96: 93-102. These publications describe the rational design of highly basic and stable mutants of the Z-domain from *S. aureus* protein A to purify different target proteins expressed in *E. coli* using cation-exchange chromatography. Use of highly basic derivatives of the Z-domain as fusion tags is also disclosed in WO 00/6343.

The present invention provides a new group of positively charged tags which can be used to purify recombinantly expressed proteins to very high purity in few steps.

SUMMARY OF THE INVENTION

In one aspect the invention is related to a method for purification of recombinant proteins comprising use of highly basic proteins from thermophilic bacteria as purification tags in a cation-exchange chromatography purification step.

In one embodiment the purification tag has a pl above about 9.

In another embodiment the purification tag has a pl above about 10.

In another embodiment the pl of the purification tag will be between about 9 and about 12.5 and in a further aspect the pl is about 10.

In one embodiment the highly basic proteins from the thermophilic bacteria are ribosomal proteins.

In one embodiment the purification tag contains no cysteine residues.

In a further embodiment the purification tag comprises from about 15 to about 250, from about 15 to about 225, from 15 to about 200, from about 15 to about 175, from about 15 to about 150, from 15 to about 75, or from about 15 to about 50 amino acid residues.

In a further embodiment the purification tag comprises from about 20 to about 120, from about 20 to about 100, from about 20 to about 90, from about 20 to about 75 amino acid residues or from about 20 to about 50 amino acid residues.

The purification tag will typically contain from at least about 15% basic amino acid residues and the purification tag may contain from about 20 to about 50%, from about 35% to about 50%, from about 20 to 30% or from about 40% to about 60% basic amino acid residues, Lys and Arg.

In another aspect the thermophilic bacteria are selected from archaebacteria or eubacteria which have growth optimum temperatures higher than about 50° C.

In one embodiment the tag will comprise a linker sequence which comprises a cleavage site for in vitro cleavage of the purification tag to give the target protein.

In another embodiment the tag is remaining on the protein after purification.

The linker may have from 1-30, from 1-25, from 1-20 or from 1-15 amino acid residues and in one embodiment the linker may comprise amino acid residues such as Leu, Pro and Ala, which increases alpha helix formation or other features resulting in structural rigidity.

The linker may be attached to either the C-terminal or the N-terminal end of the target protein.

The cleavage site may be any cleavage site which enables in vitro cleavage of the purification tag from the target protein.

Non limiting examples of cleavage sites are an enterokinase cleavage site, a Factor Xa cleavage site, a thrombin cleavage site, a Tobacco etc virus (TEV) protease cleavage site or a HRV14 3C protease cleavage site.

In one embodiment the linker may have a peptide sequence selected from the group consisting of RRGGSDDDDK (SEQ ID NO:6); SSSDDDDK (SEQ ID NO:7); SSSSTSSSSTDDDDK (SEQ ID NO:8); SSSSTLAAPFDDDDK (SEQ ID NO:9) ALAAPFDDDDK (SEQ ID NO:15), SSSSDDDDK (SEQ ID NO:16), SSSSSLEVLFQ (SEQ ID NO:17), SSSALAAPADDDDK (SEQ ID NO:18), SSSSENLYFQ (SEQ ID NO:19)

In another aspect the present invention is related to a method for making a recombinant protein comprising i) expression of a protein comprising an N-terminal or C-terminal purification tag derived from a highly basic protein from a thermophilic bacteria in a suitable expression host, ii) loading the protein on a cation-exchange column, and iii) eluting the protein with a suitable eluent.

In one embodiment the highly basic proteins are ribosomal proteins.

In a further aspect the method according to the invention will comprise a cleavage step iv) wherein the purification tag is cleaved off to give the target protein.

In one embodiment the cleavage step iv) is an enzymatic cleavage.

In a still further aspect the method according to the invention will comprise a heat precipitation step for precipitating host cell contaminants before the cation-exchange column step or at a later step eg. after enzymatic cleavage of the purification tag to precipitate the cleavage enzyme.

In one embodiment from about 30 to about 200 mM NaCl is added before the heat precipitation step.

In another embodiment from about 30 to about 100 mM NaCl is added before the heat precipitation step.

In another embodiment from about 30 to about 50 mM NaCl is added before the heat precipitation step.

In one embodiment the expression host is selected from bacteria and fungi such as *Eschericia* species, *Bacillus* species, *Saccharomyces* species and *Aspergillus* species, in particularly *Eschericia* species and *Bacillus* species.

In another aspect of the invention the purification tag is selected from the group of peptide sequences consisting of (SEQ ID NO: 1)
MSKTIVRKNESIDDALRRFKRAVSKTGTLQEVRKREFYEKPSVRRKKKSE
AARKRK;

(SEQ ID NO: 2)
MGKKTVGVKKRLAKAYKQNRRAPVWITVKTKRSVFGSPKRRHWRRSKLK
V;

(SEQ ID NO: 3)
MKRTYQPSRRKRKRTHGFLARKRTPGGRRVLKNRRRKGRWRLTV;

(SEQ ID NO: 4)
MGKGDRRTRRGKIWRGTYGKYRPRKKK
and (SEQ ID NO: 5)
MAKVKMKTNRSAAKRFKVTAKGKIKRWKSGGAHYNTKKSSKRKRHLRKHT
YVKDNMLKHVKALLKEF.

In another aspect of the invention the purification tag is selected from the group of peptide sequences consisting of (SEQ ID NO: 20)
MPKHSKRYLEARKLVDRTKYYDLDEAIELVKKTATAKFDETIELHIQTGI
DYRKPEQHIRGTIVLPHGTGKEVKVLVFAKGEKAKEALEAGADYVGAEDL
VEKIEKEGFLDFDVAIATPDMMRIIGRLGKILGPRGLMPSPKSGTVTQEV
AEAVKEFKKGRIEVRTDKTGNIHIPVGKRSFDNEKLKENIIAAIKQIMQM
KPAGVKGQFIKKVVLASTMGPGIKLNLQSLLKE, (SEQ ID NO: 21)
MAQVDLLNVKGEKVGTLEISDFVFNIDPNYDVMWRYVDMQLSNRRAGTAS
TKTRGEVSGGGRKPWPQKHTGRARHGSIRSPIWRHGGVVHGPKPRDWSKK
LNKKMKKLALRSALSVKYRENKLLVLDDLKLERPKTKSLKEILQNLQLSD
KKTLIVLPWKEEGYMNVKLSGRNLPDVKVIIADNPNNSKNGEKAVRIDGL
NVFDMLKYDYLVLTRDMVSKIEEVLGNEAGKALTA, (SEQ ID NO: 22)
MRYEYVPLKDQYEKEIVPALMKEFNYKNIHQVPKLVKIVINMGIGEGSRN
YDLIERHANELAKITGQKPIVTRARKSISNFKIRKGMPIGLKVTLRGARM
YNFLYKLINIVLPKVRDFRGLDPNSFDGRGNYSFGLSEQLVFPELNPDEV
RRIQGMDITIVTTAKTDQEARRLLELFGMPFKRG, (SEQ ID NO: 23)
MSRLAKKPIVLPQGVTVEIKDNVVKVKGPKGELSQEFLPYVKIEVEGNEV
WVRPNEEQIIRKSDWRKVKMFQGTYWSLIRNMVVGVTEGYKKELEIVGIG
YRAQLQGNTLVMNLGYAHPVVYEIPSDVKIEVPAPNRIIVSGIDKQRVGQ
VAAEIRAFRPPNVYTGKGIRYVGEVVRQKEGKKA, (SEQ ID NO: 24)
MKVILLRDVPKIGKKGEIKEVSDGYARNYLIPRGFAKEYTEGLERAIKHE
KEIEKRKKEREREESEKILKELKKRTHVVKVKAGEGGKIFGAVTAATVAE
EISKTTGLKLDKRWFKLDKPIKELGEYSLEVSLPGGVKDTIKIRVEREE, (SEQ ID NO: 25)
MLTRQQKELIVKEMSEIFKKTSLILFADFLGFTVADLTELRSRLREKYGD
GARFRVVKNTLLNLALKNAEYEGYEEFLKGPTAVLYVTEGDPVEAVKIIY
NFYKDKKADLSRLKGGFLEGKKFTAEEVENIAKLPSKEELYAMLVGRVKA
PITGLVFALSGILRNLVYVLNAIKEKKSE, (SEQ ID NO: 26)
MARYFPVQKTTMIKPEEVERKWYVVDASGKVLGRLATRIAKILMGKHKPN
YTPHVDTGDYVIVVNADKVVLTGKKLDQKVYYWHSGYPGGLKSLTARQML
EKHPERLIWLAVKRMLPKNRKGRKMLKRLKVYASPEHPHQAQKPEPIEL, (SEQ ID NO: 27)
MRLEDLRPTPGAMKKRKRVGRGPGSGHGKTSGRGHKGQKARGSGKVHIWF
EGGQTPLQRRLPKRGFKNINKKVYAVVNVKVLEERFEANEEVTPEKLIER
KIIKDLKDGVKILGDGELTKPLVVKAHAFSKSAVEKIESAGGKAEVI, (SEQ ID NO: 28)
MRHRVKRHKLGRYGSHRKSLLRNLSREIVEHGSIVTTTAKAKALKTFMDK
LVSKAIEAATTDDRARSVHLRRQINAVLGDRRLTNKLVDEIAKNYVGRRG
GYVRVLRIGFRRGDAAEMSLVQLVEASSQEG, (SEQ ID NO: 29)
MDHLVKIIEKKYEKKEIPDFRPGDTVRVHVKVIEGDRERTQVFEGIVIAK
RGSGINKTFTVRRIGSHGVGVERIFPVHSPVVEKIEVVRKGKVRRAKLYY
LRNVRGKIRIKERRD, -continued (SEQ ID NO: 30)
MRVKRAVHAKKKRKKYLKAAKGYRGALSRRYKLAKQMYVRSKWYSYVGRK
QKKRDMRKLWITRINIAARNEGLKYSELIHGLKLAGVSINRKMLSELAVN
DPEAFKEYVKIAKEALAS, (SEQ ID NO: 31)
MLYAIVETAGRQYRVEEGKILYTEKQKDYSPGDEIVFDRVVFVRKDGEVL
VGKPYVEGAKVVGKVLEHAKARKVKTVKYRPRKNSKVEKGHRQWYTAIKI
EKIEL, (SEQ ID NO: 32)
MKQEKLSLHDVLIRPIITEKALILREQRKYVFEVNPLANKNLVKEAVEKL
FNVKVEKVNILNMKPKPKRRGIFEGKTRSWKKAVVTLKEGYTIKELEGE
H, (SEQ ID NO: 33)
MAHKKSGGVAKNGRDSLPKYLGVKVGDGQIVKAGNILVRQRGTRFYPGKN
VGMGRDFTLFALKDGRVKFETKNNKKYVSVYEE, (SEQ ID NO: 34)
MKASELRNYTDEELKNLLEEKKRQLMELRFQLAMGQLKNTSLIKLTKRDI
ARIKTILRERELGIRR, (SEQ ID NO: 35)
MPKKLKIKLVKSPIGYSWDQKDTVKRLGLKKLNQVVIKDDLPQIRGMIRK
VKHLVEVEEIEEGGSNA, (SEQ ID NO: 36)
MKRTYQPSRRKRKRTHGFLARKRTPGGRRVLKNRRRKGRWRLTV, (SEQ ID NO: 37)
MPKVKTNRSAAKRFRITKNGKIMRNHAYRSHKTGKKRRNALRALRKKDVV
SSADKNRVLRLLGKK, (SEQ ID NO: 38)
MGQKVHPRGFRLGLSADWQAKWFNEKNYKEWLLEDEEIRKIIKNKYYHAG
ISEIYVERPDAERINITVKTARPGIIIGRKGSEITSLREELERKFNRRVV
INIEEIKTPELDAQLVAESIASRIEKRASYKVAMKRAIMNAMRKGAQGIK
VMVAGRLGGAEIARREWYLRGRLPLQKIKAIIDYGTATAWTKYGTIGIKV
WIYKGDADI, (SEQ ID NO: 39)
METQGVMKEIQYEEFEEKIIEIRRTSKVTKGGKNLSFRVVAIVGNKNGKV
GLGIGKAREVPEAIRKAISAAKRNIVEVPVINGTIPHEVIGRQDASKVLL
KPAAPGTGIIAGGTVRAVVELAGIQNILTKSLGSTNPLNLALATMNGLKN
LLDPRKVAKLRDISVEEVFKGVRRENNA, (SEQ ID NO: 40)
MVSLDPEKKNEIIKEFQIHENDTGSVEVQIALLTARIKHLTEHLRKHPKD
FHSRRGLMKMIGRRRKMLKYLRHKKPEVYRELIAKLGIRK, (SEQ ID NO: 41)
MGRSRKKGPYVDRKLLEKIRKLNETGEKKVIKTWSRASMIIPEMVGHTIA
VYNGMKHIPVYITENMIGHRLGEFAPTRRFGGHADKKAKKGELKK
and (SEQ ID: NO 42)
MPNIKSAKKRVRVSEKRRLRNKAYKTFFKNRIKEVLKAIENKEPKEVVLE
LTRKAQAAIDKAVSKGVIHKNQGARRKARLFEKVNEYLRTLETTQE.

In another embodiment the purification tag is selected from the group consisting of (SEQ ID NO: 32)
MKQEKLSLHDVLIRPIITEKALILREQRKYVFEVNPLANKNLVKEAVEKL
FNVKVEKVNILNMKPKPKRRGIFEGKTRSWKKAVVTLKEGYTIKELEGEH
and (SEQ ID NO: 33)
MAHKKSGGVAKNGRDSLPKYLGVKVGDGQIVKAGNILVRQRGTRFYPGKN
VGMGRDFTLFALKDGRVKFETKNNKKYVSVYEE.

The target protein will typically be of a size from about 20 to about 400 amino acid residues, more typically from about 30 to about 400 amino acid residues or from about 30 to about 400 amino acid residues.

In a further aspect of the invention the target protein is selected from human proteins and their analogues such as aprotinin, tissue factor pathway inhibitor or other protease inhibitors, insulin or insulin analogues, human or bovine growth hormone, interleukin, glucagon, GLP-1, GLP-2, IGF-I, IGF-II, tissue plasminogen activator, transforming growth factor α or β, platelet-derived growth factor, GRF (growth hormone releasing factor), immunoglubolines, EPO, TPA, protein C, blood coagulation factors such as FVII, FVIII, FIV and FXIII, exendin-3, exentidin-4, and enzymes or functional analogues thereof.

DESCRIPTION OF THE DRAWINGS

FIG. 3 discloses the chromatogram of a NNC20 where

DESCRIPTION OF THE INVENTION

Figure 1:
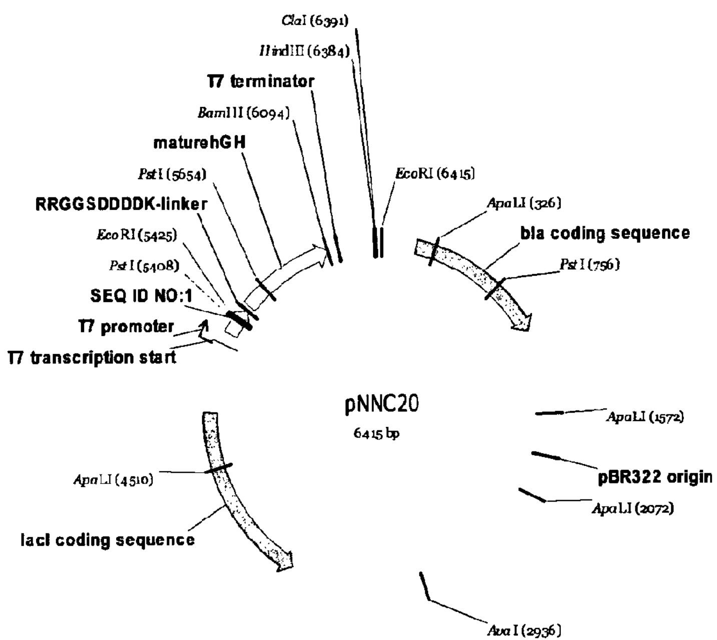
FIG. 1 discloses an expression vector pNNC20 comprising the following elements; lacI coding sequence, ampicillin (bla) coding sequence, pBR322 origin of replication, T7 promoter region, T7 terminator region, SEQ ID NO:1 purification tag, RRGGSDDDDK (SEQ ID NO:6) linker region and mature human hGH sequence.

Strains of thermophilic bacteria have been identified with optimum temperatures ranging from ~50° C. to above the boiling point of water. The strains that survive at extremely high temperatures are called hyperthermophiles or thermophiles and have a temperature optimum of 80° C. (176° F.) or higher. Thermophilic bacteria occur naturally in hot springs, hot soils, geothermal vents and other places were high temperature are present. *Bacillus stearothermophillus* from which RS21_BACST (SEQ ID NO:1) was cloned and used as a tag is for example found to grow above 65° C. in many soils. In order to survive the high temperatures, these organisms have evolved proteins which are more stable than those of mesophiles.

The purification tags according to the present invention are derived from thermophilic bacteria and are in general soluble, highly stable and have a very basic pl due to a large amount of Arg and Lys residues present in the amino acid sequence. The solubility is believed to be derived from the generally high surface charge of the proteins. The purification tags according to the present invention comprise a high percentage of positively charged amino acid residues Lys and Arg.

Representative examples of species comprising thermophiles are *Acetomicrobium* sp., *Acidianus* sp.; *Acremonium* sp.; *Actinopolyspora* sp.; *Aeropyrum* sp.; *Alicyclobacillus* sp., *Ammonifex* sp.; *Amycolatopsis* sp.; *Anaerobaculum* sp.; *Anaerobranca* sp.; *Anaerocellum* sp.; *Aneurinibacillus* sp.; *Anoxybacillus* sp.; *Aquifex* sp.; *Archaeoglobus* sp.; *Bacillus* sp.; *Brevibacillus* sp.; *Caldicellulosiruptor* sp.; *Caldithrix* sp.; *Caldivirga* sp.; *Caloramator* sp.; *Caloranaerobacter* sp.; *Caminibacter* sp.; *Carboxydothermus* sp.; *Chaetomium* sp.; *Chlorobaculum* sp.; *Chloroflexus* sp.; *Clostridium* sp.; *Coprothermobacter* sp.; *Deferribacter* sp.; *Deinococcus* sp.; *Desulfacinum* sp.; *Desulfotomaculum* sp.; *Desulfurella* sp.; *Desulfurococcus* sp.; *Dictyoglomus* sp.; *Ferroglobus* sp.; *Fervidobacterium* sp.; *Gelria* sp.; *Geobacillus* sp.; *Halorhodospira* sp.; *Halothermothrix* sp.; *Heliobacterium* sp.; *Hippea* sp.; *Hydrogenobacter* sp.; *Hydrogenophilus* sp.; *Hyperthermus* sp.; *Malbranchea* sp.; *Marinitoga* sp.; *Meiothermus* sp.; *Metallosphaera* sp.; *Methanobacterium* sp.; *Methanocaldococcus* sp.; *Methanoculleus* sp.; *Methanohalobium* sp.; *Methanopyrus* sp.; *Methanosarcina* sp.; *Methanothermobacter* sp.; *Methanothermococcus* sp.; *Methanothermus* sp.; *Methanothrix* sp.; *Methanotorris* sp.; *Microbispora* sp.; *Moorella* sp.; *Myceliophthora* sp.; *Nautilia* sp.; *Palaeococcus* sp.; *Pelotomaculum* sp.; *Persephonella* sp.; *Petrotoga* sp.; *Picrophilus* sp.; *Pseudomonas* sp.; *Pseudonocardia* sp.; *Pyrobaculum* sp.; *Pyrococcus* sp.; *Pyrodictium* sp.; *Rhizomucor* sp.; *Rhizomucor* sp.; *Rhodothermus* sp.; *Roseiflexus* sp.; *Rubrobacter* sp.; *Saccharococcus* sp.; *Saccharomonospora* sp.; *Saccharopolyspora* sp.; *Scytalidium* sp.; *Spirochaeta* sp.; *Stetteria* sp.; *Streptomyces* sp.; *Stygiolobus* sp.; *Sulfobacillus* sp.; *Sulfolobus* sp.; *Sulfophobococcus* sp.; *Sulfurihydrogenibium* sp.; *Syntrophothermus* sp.; *Tepidimonas* sp.; *Thermacetogenium* sp.; *Thermaerobacter* sp.; *Thermanaerovibrio* sp.; *Thermicanus* sp.; *Thermoactinomyces* sp.; *Thermoanaerobacter* sp.; *Thermoanaero-bacterium* sp.; *Thermoanaerobium* sp.; *Thermoanaeromonas* sp.; *Thermoascus* sp.; *Thermo-bifida* sp.; *Thermobrachium* sp.; *Thermochromatium* sp.; *Thermococcus* sp.; *Thermodesulfo-vibrio* sp.; *Thermodesulfobacterium* sp.; *Thermodesulforhabdus* sp.; *Thermo-filum* sp.; *Thermohydrogenium* sp.; *Thermomonospora* sp.; *Thermonema* sp.; *Therm-oplasma* sp.; *Thermoproteus* sp.; *Thermosipho* sp.; *Thermosphaera* sp.; *Thermo-syntropha* sp.; *Thermo-terrabacterium* sp.; *Thermotoga* sp.; *Thermovenabulum* sp.; *Thermo-vibrio* sp.; *Thermus* sp. and *Ureibacillus* sp.

The present purification method can be used to purify a large number of proteins being produced by recombinant gene technology. The target protein is typically of small to medium size and may have up to about 400 amino acid residues. The target proteins may be of a size from about 30 to about 400 amino acid residues, from about 40 to about 400 amino acid residues, from about 50 to about 400 amino acid residues, from about 60 to about 400 amino acid residues, from about 70 to about 400 amino acid residues, from about 80 to about 400 amino acid residues, from about 90 to about 400 amino acid residues or from about 100 to about 400 amino acid residues.

Further, the target protein may be of from about 30 to about 300 amino acid residues, from about 40 to about 300 amino acid residues, from about 50 to about 300 amino acid residues, from about 60 to about 300 amino acid residues, from about 70 to about 300 amino acid residues, from about 80 to about 300 amino acid residues, from about 90 to about 300 amino acid residues or from about 100 to about 300 amino acid residues.

Further, the target protein may be of from about 30 to about 200 amino acid residues, from about 40 to about 200 amino acid residues, from about 50 to about 200 amino acid residues, from about 60 to about 200 amino acid residues, from about 70 to about 200 amino acid residues, from about 80 to about 200 amino acid residues, from about 90 to about 200 amino acid residues or from about 100 to about 200 amino acid residues.

Further, the target protein may be of from about 30 to about 100 amino acid residues, from about 40 to about 100 amino acid residues, from about 50 to about 100 amino acid residues, from about 60 to about 100 amino acid residues, from about 70 to about 100 amino acid residues, from about 80 to about 100 amino acid residues or from about 90 to about 100 amino acid residues.

Non limiting examples of such proteins are: aprotinin, tissue factor pathway inhibitor or other protease inhibitors, insulin or insulin precursors, human or bovine growth hormone, interleukin, glucagon, GLP-1, GLP-2, IGF-I, IGF-II, tissue plasminogen activator, transforming growth factor α or β, platelet-derived growth factor, GRF (growth hormone releasing factor), immunoglubolines, EPO, TPA, protein C, blood coagulation factors such as FVII, FVIII, FIV and FXIII, exendin-3, exentidin-4, and enzymes or functional analogues thereof.

Other examples of target proteins are transforming growth factor α (TGF-α), transforming growth factor β (TGF-β), epidermal growth factor (EGF), vascular endothelial growth factor (VEGF), thrombopoietin (TPO), interferon, pro-urokinase, urokinase, plasminogen activator inhibitor 1, plasminogen activator inhibitor 2, von Willebrandt factor, a cytokine, e.g. an interleukin such as interleukin (IL) 1, IL-1Ra, IL-2, IL-4, IL-5, IL-6, IL-9, IL-11, IL-12, IL-13, IL-15, IL-16, IL-17, IL-18, IL-20 or IL-21, a colony stimulating factor (CFS) such as GM-CSF, stem cell factor, a tumor necrosis factor such as TNF-α, lymphotoxin-α, lymphotoxin-β, CD40L, or CD30L, a protease inhibitor e.g. aprotinin, an enzyme such as superoxide dismutase, asparaginase, arginase, arginine deaminase, adenosine deaminase, ribonuclease, catalase, uricase, bilirubin oxidase, trypsin, papain, alkaline phosphatase, β-glucoronidase, purine nucleoside phosphorylase or batroxobin, an opioid, e.g. endorphins, enkephalins or non-natural opioids, a hormone or neuropeptide, e.g. calcitonin, glucagon, gastrins, adrenocorticotropic hormone (ACTH), cholecystokinins, lutenizing hormone, gonadotropin-releassing hormone, chorionic gonadotropin, corticotrophin-releasing factor, vasopressin, oxytocin, antidiuretic hormones, thyroid-stimulating hormone, thyrotropin-releasing hormone, relaxin, prolactin, peptide YY, neuropeptide Y, pancreastic polypeptide, leptin, CART (cocaine and amphetamine regulated transcript), a CART related peptide, perilipin, melanocortins (melanocyte-stimulating hormones) such as MC-4, melanin-concentrating hormones, natriuretic peptides, adrenomedullin, endothelin, secretin, amylin, vasoactive intestinal peptide (VIP), pituary adenylate cyclase activating polypeptide (PACAP), bombesin, bombesin-like peptides, thymosin, heparin-binding protein, soluble CD4, hypothalmic releasing factor and melanotonins.

In another embodiment of the invention the target protein may be insulin receptor agonist or antagonist peptides or other peptides designed to interact with other cell membrane receptors In another embodiment of the invention the target protein may be a processing enzyme such as proteases (eg enterokinase, caspases trypsine like serine proteases), lipase, phospatase, glycosyl hydrolases (eg. mannosidases, xylosidases, fucosidases), kinase, mono or dioxidase, peroxidase, transaminase, carboxypeptidase, amidase, esterase, and phosphatase.

Thermostable proteins are often stabilized through salt bridging, by increased number of hydrogen bonds and a very compact packing of the hydrophobic core. Thus, the structural integrity of proteins from thermophilic bacteria is believed to be mediated via intra-molecular interactions even in proteins without cysteine residues. The absence of cysteine residues in a purification tag is advantageous as this will reduce the risk of interferences from cysteine residues in the purification tag with disulphide bridges in the target protein and reduce the formation of insoluble disulphide linked aggregates during protein expression. The high charge of the purification tag will also contribute to the solubility of the fusion protein. The susceptibility of a peptide bond to cleavage by a protease is determined by both the flexibility of the protein chain region in which it is located, the extent to which the bond is exposed, and how local interactions are made by the side chains of its flanking residues. Each of these parameters is influenced by the overall structural stability of the protein. Thus, the structural integrity of the purification tag according to the present invention will limit the potential degradation of the tag by trypsin like proteases from the host cell used for production of the fusion protein.

A number of tagged proteins were cloned and expressed *E. coli*. The tagged proteins were expressed without significant degradation of the purification tag and only very few contaminant peptides were found after cleavage with trypsin. Thus, the tag has a high resistance towards trypsin-like proteases and ensures effective cleavage of the expressed tagged protein. Furthermore, it was found that the purification tag did not interfere with the establishment of the correct disulphide bridges in the target protein.

In *E. coli* the majority of abundant proteins are found in a pl cluster ranging from pl 4-7 and 8-10 in which the majority of the proteins as well as the most abundant proteins are found in the pl 4-7 range. The purification tags according to the invention are highly alkaline and will when fused to a target protein significantly increase the overall positive charge and pl of the fusion protein so that it is clearly distinguished from the major bulk of host cell contaminants. This will allow the fusion protein to be eluted at salt concentrations or at a pl at which the host cell contaminants will not be able to bind to a given cation exchange matrix.

Any suitable cation exchange matrix can be used in the method according to the invention and a non limiting list of suitable cation exchange column material is: SP-Sepharose XL Amersham cat no 17-5073-01; Streamline SP XL Amersham cat no 17-5076-01; Streamline Direct CST Amersham cat no 17-5266-03; Obelix SP Amersham cat no 11-0010-86; S-Support Unosphere, BioRad cat no 156-0113; SP-Sepharose High Performance Amersham cat no 17-1087-03; Source30S Amersham cat no 17-1273-02 and Toyopearl SP650S TosoHaas cat no 08437

The purification tags according to the invention will contribute differently to the overall charge of a specific target protein depending on the pI and charge of the chosen purification tag. Thus, purification of a specific target protein can be optimized by choosing a purification tag which enables elution of the fusion protein at a salt concentration or at a pH at which only minimal amounts of the host cell contaminants will co-elute.

The amino acid residues in the linker can be selected from such amino acid residues which will provide a less flexible structure to the tagged protein. Hereby the interference between the target protein and the purification tag may be minimized. In one embodiment, the linker may comprise structural elements such as alpha helix structure.

The expressed tagged or fusion proteins produced by the cells may be recovered from the culture medium by conventional procedures including separating the host cells from the medium by centrifugation or filtration, releasing the fusion protein by mechanical cell disruption, such as ultrasonication or pressure, precipitating the protein aqueous components of the supernatant or filtrate by means of a salt, e.g. ammonium sulphate. Due to the thermostbility of the purification tags according to the invention a prechromatographic step comprising a heat precipitation of host cell contaminants is also possible, especially if the target protein is small in comparison to the fusion tag. After sonication a suitable concentration of NaCl can be added to further decrease the ability of host cell contaminants to bind to the cation exchange matrix. After cation-exchange chromatography the fusion protein may be eluted in a salt gradient and eluate fractions containing the fusion protein were collected.

Purity of the fusion protein was evaluated by analyzing Coomasie stained PAGE gels using gel image analysis software.

After the first purification step the purification tag can be cleaved off directly with a suitable processing enzyme (eg. EK). If the salt concentration is too high the fusion protein may be desalted before cleavage. The cleavage site can be any cleavage site which will enable efficient in vitro cleavage after isolating the purified fusion protein. The most commonly used enterokinase cleavage site has the sequence DDDDK (SEQ ID NO:10), where cleavage occurs after K. Other non-limiting processing enzymes cleavage sites include the Factor Xa cleavage site, which is most commonly IEGR (SEQ ID NO:11), where cleavage occurs after R; the thrombin cleavage site, which is most commonly LVPRG (SEQ ID NO:12) or LVPRGS (SEQ ID NO:13) where cleavage occurs after the R; the Tobacco etcs virus (TEV) protease cleavage site, which is most commonly ENLYFQG/S (SEQ ID NO:14), where cleavage occurs after Q and the HRV14 3C protease cleavage site, which is most commonly LEVLFQ/GP (SEQ ID NO: 45) where cleavage occurs after Q.

The steps following cleavage may include a further cation exchange column purification as in the first step. In such scenario the purification tag released by the processing enzyme will have an extremely high pI leading to very efficient binding to the cation exchange matrix. The cleaved protein can now be collected in the flow through from the column, whereas the cleaved off purification tag and remaining highly charged contaminants from the production cell line will be retained on the cation exchange column.

Purification steps following cleavage may also comprise other means of purification such as anion exchange chromatography, hydrophobic interaction chromatography and gel filtration chromatography (see, for example, Scopes, R., Protein Purification, Springer-Verlag, N.Y., 1982).

For therapeutic purposes the target protein has to be substantially pure after the last purification step. Thus, in a preferred embodiment of the invention the target protein is purified to at least about 90 to 95% homogeneity, preferably to at least about 98% homogeneity. Purity may be assessed by e.g. gel electrophoresis, amino acid analysis or other HPLC based methods.

The nucleic acid construct encoding the fusion protein may suitably be of genomic or cDNA origin, for instance obtained by preparing a genomic or cDNA library and screening for DNA sequences coding for all or part of the fusion protein by hybridization using synthetic oligonucleotide probes in accordance with standard techniques (cf. Sambrook et al., Molecular Cloning: A Laboratory Manual, 2nd. Ed. Cold Spring Harbor Labora-tory, Cold Spring Harbor, N.Y., 1989).

The nucleic acid construct encoding the fusion protein may also be prepared synthetically by established standard methods, e.g. the phosphoamidite method described by Beaucage and Caruthers, Tetrahedron Letters 22 (1981), 1859-1869, or the method described by Matthes et al., EMBO Journal 3 (1984), 801-805. According to the phosphoamidite method, oligonucleotides are synthesised, e.g. in an automatic DNA synthesiser, purified, annealed, ligated and cloned in suitable vectors. The DNA sequences encoding the fusion protein may also be prepared by polymerase chain reaction such as splicing by overlap extension PCR using specific primers, for instance as described in U.S. Pat. No. 4,683,202, Saiki et al., Science 239 (1988), 487-491, or Sambrook et al., supra.

Furthermore, the nucleic acid construct may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire nucleic acid construct, in accordance with standard techniques.

The DNA sequences encoding the fusion protein are usually inserted into a recombinant vector which may be any vector, which may conveniently be subjected to recombinant DNA procedures, and the choice of vector will often depend on the host cell into which it is to be introduced. Thus, the vector may be an autonomously replicating vector, i.e. a vector, which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the fusion protein is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the fusion protein.

Expression vectors for use in expressing the fusion protein will comprise a promoter capable of directing the transcription of a cloned gene or cDNA. The promoter may be any DNA sequence, which shows transcriptional activity in the host cell of choice and may be derived from genes encoding proteins either homologous or heterologous to the host cell.

Examples of suitable promoters for directing the transcription of the DNA in mammalian cells are the SV40 promoter (Subramani et al., Mol. Cell. Biol. 1 (1981), 854-864), the MT-1 (metallothionein gene) promoter (Palmiter et al., Science 222 (1983), 809-814), the CMV promoter (Boshart et al., Cell 41:521-530, 1985) or the adenovirus 2 major late promoter (Kaufman and Sharp, Mol. Cell. Biol, 2:1304-1319, 1982).

Examples of suitable promoters for use in yeast host cells include promoters from yeast glycolytic genes (Hitzeman et al., J. Biol. Chem. 255 (1980), 12073-12080; Alber and Kawasaki, J. Mol. Appl. Gen. 1 (1982), 419-434) or alcohol dehydrogenase genes (Young et al., in Genetic Engineering of Microorganisms for Chemicals (Hollaender et al, eds.), Plenum Press, New York, 1982), or the TPI1 (U.S. Pat. No. 4,599,311) or ADH2-4c (Russell et al., Nature 304 (1983), 652-654) promoters.

Examples of suitable promoters for use in filamentous fungus host cells are, for instance, the ADH3 promoter (McKnight et al., The EMBO J. 4 (1985), 2093-2099) or the tpiA promoter. Examples of other useful promoters are those derived from the gene encoding *A. oryzae* TAKA amylase, *Rhizomucor miehei* aspartic proteinase, *A. niger* neutral alpha-amylase, *A. niger* acid stable alpha-amylase, *A. niger* or *A. awamori* glucoamylase (gluA), *Rhizomucor miehei* lipase, *A. oryzae* alkaline protease, *A. oryzae* triose phosphate isomerase or *A. nidulans* acetamidase. Preferred are the TAKA-amylase and gluA promoters. Suitable promoters are mentioned in, e.g. EP 238 023 and EP 383 779.

Examples of suitable promoters for use in bacterial host cells include the promoter of the *Bacillus stearothermophilus* maltogenic amylase gene, the *Bacillus licheniformis* alpha-amylase gene, the *Bacillus amyloliquefaciens* BAN amylase gene, the *Bacillus subtilis* alkaline protease gen, or the *Bacillus pumilus* xylosidase gene, or the phage Lambda $P_R$ or $P_L$ promoters or promoters used for expression in *E. coli* eg. lac, trp, phoA, araBAD, tac, bacteriophage T7 and cspA.

The vector may also comprise a selectable marker, e.g. a gene product which complements a defect in the host cell, such as the gene coding for dihydrofolate reductase (DHFR) or the *Schizosaccharomyces pombe* TPI gene (described by P. R. Russell, Gene 40, 1985, pp. 125-130), or a marker gene which confers resistance to a drug, e.g. ampicillin, kanamycin, tetracyclin, chloramphenicol, neomycin, hygromycin or methotrexate. For filamentous fungi, selectable markers include amdS, pyrG, argB, niaD and sC.

The DNA sequences encoding the fusion protein may also, if necessary, be operably connected to a suitable terminator, such as the human growth hormone terminator (Palmiter et al., Science 222, 1983, pp. 809-814) or the TPI1 (Alber and Kawasaki, J. Mol. Appl. Gen. 1, 1982, pp. 419-434) or ADH3 (McKnight et al., The EMBO J. 4, 1985, pp. 2093-2099) terminators. Expression vectors may also contain a set of RNA splice sites located downstream from the promoter and upstream from the insertion site for the fusion polypeptide sequence itself. Preferred RNA splice sites may be obtained from adenovirus and/or immunoglobulin genes. Also contained in the expression vectors is a polyadenylation signal located downstream of the insertion site. Particularly preferred polyadenylation signals include the early or late polyadenylation signal from SV40 (Kaufman and Sharp, ibid.), the polyadenylation signal from the adenovirus 5 Elb region, the human growth hormone gene terminator (DeNoto et al. Nucl. Acids Res. 9:3719-3730, 1981). The expression vectors may also include a non coding viral leader sequence, such as the adenovirus 2 tripartite leader, located between the promoter and the RNA splice sites; and enhancer sequences, such as the SV40 enhancer.

To direct the fusion protein into the secretory pathway of the host cells, a secretory signal sequence (also known as a leader sequence, prepro sequence or pre sequence) may be provided in the recombinant vector. The secretory signal sequence is joined to the DNA sequences encoding the fusion protein in the correct reading frame. Secretory signal sequences are commonly positioned 5' to the DNA sequence encoding the peptide. The secretory signal sequence may be that, normally associated with the protein or may be from a gene encoding another secreted protein.

For secretion from yeast cells, the secretory signal sequence may encode any signal peptide, which ensures efficient direction of the expressed polypeptides into the secretory pathway of the cell. The signal peptide may be naturally occurring signal peptide, or a functional part thereof, or it may be a synthetic peptide. Suitable signal peptides have been found to be the alpha-factor signal peptide (cf. U.S. Pat. No. 4,870,008), the signal peptide of mouse salivary amylase (cf. O. Hagenbuchle et al., Nature 289, 1981, pp. 643-646), a modified carboxypeptidase signal peptide (cf. L. A. Valls et al., Cell 48, 1987, pp. 887-897), the yeast BAR1 signal peptide (cf. WO 87/02670), or the yeast aspartic protease 3 (YAP3) signal peptide (cf. M. Egel-Mitani et al., Yeast 6, 1990, pp. 127-137).

For efficient secretion in yeast, a sequence encoding a leader peptide may also be inserted downstream of the signal sequence and upstream of the DNA sequence encoding the polypeptides. The function of the leader peptide is to allow the expressed peptide to be directed from the endoplasmic reticulum to the Golgi apparatus and further to a secretory vesicle for secretion into the culture medium (i.e. exportation of the polypeptides across the cell wall or at least through the cellular membrane into the periplasmic space of the yeast cell). The leader peptide may be the yeast alpha-factor leader (the use of which is described in e.g. U.S. Pat. No. 4,546,082, U.S. Pat. No. 4,870,008, EP 16 201, EP 123 294, EP 123 544 and EP 163 529). Alternatively, the leader peptide may be a synthetic leader peptide, which is to say a leader peptide not found in nature. Synthetic leader peptides may, for instance, be constructed as described in WO 89/02463 or WO 92/11378.

For use in filamentous fungi, the signal peptide may conveniently be derived from a gene encoding an *Aspergillus* sp. amylase or glucoamylase, a gene encoding a *Rhizomucor miehei* lipase or protease or a *Humicola lanuginosa* lipase. The signal peptide is preferably derived from a gene encoding *A. oryzae* TAKA amylase, *A. niger* neutral alpha-amylase, *A. niger* acid-stable amylase, or *A. niger* glucoamylase. Suitable signal peptides are disclosed in, e.g. EP 238 023 and EP 215 594.

The host cell into which the DNA construct encoding the fusion protein is introduced may be any cell which is capable of producing the present fusion polypeptides and includes bacteria, yeast, fungi and higher eukaryotic cells.

Examples of bacterial host cells which, on cultivation, are capable of producing the polypeptide of the invention are grampositive bacteria such as strains of *Bacillus*, such as strains of *B. subtilis, B. licheniformis, B. lentus, B. brevis, B. stearothermophilus, B. alkalophilus, B. amyloliquefaciens, B. coagulans, B. circulans, B. lautus, B. megatherium* or *B. thuringiensis*, or strains of *Streptomyces*, such as *S. lividans* or *S. murinus*, or gramnegative bacteria such as strains of *Echerichia coli*. The transformation of the bacteria may be effected by protoplast transformation or by using competent cells in a manner known per se (cf. Sambrook et al., supra).

When expressing protein in bacteria such as *E. coli*, the protein may be retained in the cytoplasm, typically as insoluble granules (known as inclusion bodies), or may be directed to the periplasmic space by a bacterial secretion sequence. In the former case, the cells are lysed and the granules are recovered and denatured after which the polypeptide is refolded by diluting the denaturing agent. In the latter case, the target protein may be cloned with a strong signal peptide sequence such as phoA, degQ, degS, degP, OmpA, OmpF, OmpH, OmpP, OmpT, Iamb or pelB (from *Erwania carotovora*) and the polypeptide may be recovered from the periplasmic space by disrupting the cells, e.g. by sonication or osmotic shock, to release the contents of the periplasmic space and recovering the polypeptide.

Examples of suitable yeasts cells include cells of *Saccharomyces* spp. or *Schizosac-charomyces* spp., in particular strains of *Saccharomyces cerevisiae* or *Saccharomyces kluyveri*. Methods for transforming yeast cells with heterologous DNA and producing heterologous poly-peptides there from are described, e.g. in U.S. Pat. No. 4,599,311, U.S. Pat. No. 4,931,373, U.S. Pat. Nos. 4,870,008, 5,037,743, and U.S. Pat. No. 4,845,075, all of which are hereby incorporated by reference. Transformed cells are selected by a phenotype determined by a selectable marker, commonly drug resistance or the ability to grow in the absence of a particular nutrient, e.g. leucine. A preferred vector for use in yeast is the POT1 vector disclosed in U.S. Pat. No. 4,931,373. The DNA sequences encoding the human polypeptides may be preceded by a signal sequence and optionally a leader sequence, e.g. as described above. Further examples of suitable yeast cells are strains of *Kluyveromyces*, such as *K. lactis, Hansenula*, e.g. *H. polymorpha*, or *Pichia*, e.g. *P. pastoris* (cf. Gleeson et al., J. Gen. Microbiol. 132, 1986, pp. 3459-3465; U.S. Pat. No. 4,882,279).

Examples of other fungal cells are cells of filamentous fungi, e.g. *Aspergillus* spp., *Neurospora* spp., *Fusarium* spp. or *Trichoderma* spp., in particular strains of *A. oryzae, A. nidulans* or *A. niger*. The use of *Aspergillus* spp. for the expression of proteins is described in, e.g., EP 272 277, EP 238 023, EP 184 438 The transformation of *F. oxysporum* may, for instance, be carried out as described by Malardier et al., 1989, Gene 78: 147-156. The transformation of *Trichoderma* spp. may be performed for instance as described in EP 244 234.

When a filamentous fungus is used as the host cell, it may be transformed with the DNA construct of the invention, conveniently by integrating the DNA construct in the host chromosome to obtain a recombinant host cell. This integration is generally considered to be an advantage as the DNA sequence is more likely to be stably maintained in the cell. Integration of the DNA constructs into the host chromosome may be performed according to conventional methods, e.g. by homologous or heterologous recombination.

The transformed or transfected host cell is then cultured in a suitable nutrient medium under conditions permitting expression of the fusion protein after which all or part of the resulting peptide may be recovered from the culture. The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection).

DEFINITIONS

In the present context "Thermophilic microorganisms" means organisms which grow optimally at about 50° C. to about 100° C. This is in contrast to mesophiles which in general grow optimally at temperatures from 30-37° C. The term "thermophilic bacteria" will in this context cover hyperthermophilic bacteria as well.

"Ribosomal proteins" are peptide or polypeptide subunits of the ribosome which are the particles that catalyze mRNA-directed protein synthesis in all organisms. Ribosomal proteins are defined on the basis of their sequence by ribosomal signatures as reported in domain databases such as InterPro and Prosite.

"Recombinant protein" is a protein produced by recombinant production technology.

The expression "purification tag" means a peptide sequence fused to a target protein either at the N- or C-terminal end of the target protein and used for purification according to the present invention.

The expression "Target protein" means the ultimate protein of interest. Thus the target protein may be the expressed fusion protein or, more typically, it will be protein isolated after the purification tag has been cleaved of.

The expression "Fusion protein" or "tagged" protein" means a protein having a purification tag attached to either the C-terminal or the N-terminal end of the target protein.

"hGH" mean mature human growth hormone consisting of the 1-191 amino acids in human growth hormone.

"hGH-Leu-Ala mean mature human growth hormone with a C-terminal Leu-Ala extension With the expression "a highly basic protein" is meant a protein having a high percent of the basic amino acid residues Lys and Arg, e.g. at least about 15% of the total number of amino acid residues in the protein.

"Application" means a sample containing the fusion protein which is loaded on a purification column.

"Flow through" means the part of the application containing host cell proteins and contaminants which do not bind to the purification column "Main peak" refers to the peak in a purification chromatogram which has the highest UV intensity and which contains the fusion protein "mAU" is milliabsorbance units.

"UV 280 intensity" is the absorbance at a wavelength of 280 nm at which proteins will absorb, measured in milliabsorbance units "IPTG" is isopropyl-β-D-thiogalactopyranoside.

EK is enterokinase

TIC is Total Ion Count

With the expression "linker" is meant an amino acid sequence linking the purification tag and the target protein together. The linker sequence may comprise a sequence which promotes better folding of the target protein and/or a cleavage site for cleaving off the purification tag.

A "helix structure" is characterized by having an amino acid sequence which results in a coiled structure stabilized by interchain hydrogen bonds.

The expression "protein" will cover both peptides and polypeptides.

"% Solubility" is defined as the amount of soluble fusion protein from host cell lysate divided by amount of soluble+insoluble fusion protein from host cell lysate×100.

"% Purity" is defined as the amount of the protein of interest divided by the amount of protein of interest+the amount of host cell contaminants×100.

SOE PCR means Splicing by overlap extension PCR.

LC-MS refers to liquid chromatography mass spectrometry.

In the present context, the term "functional analogue" is meant to indicate a protein with a similar function as the fusion protein native protein. The protein may be structurally similar to the native protein and may be derived from the native protein by addition of one or more amino acids to either or both the C- and N-terminal end of the native protein, substitution of one or more amino acids at one or a number of different sites in the native amino acid sequence, deletion of one or more amino acids at either or both ends of the native protein or at one or several sites in the amino acid sequence, or insertion of one or more amino acids at one or more sites in the native amino acid sequence. Thus an insulin analogue is an insulin molecule having one or more mutations, substitutions, deletions and or additions of the A and/or B amino acid chains relative to the human insulin molecule. The insulin analogues are preferably such wherein one or more of the naturally occurring amino acid residues, preferably one, two, or three of them, have been substituted by another codable amino acid residue. Thus position 28 of the B chain may be modified from the natural Pro residue to one of Asp, Lys, or Ile. In another embodiment Lys at position B29 is modified to Pro; Also, Asn at position A21 may be modified to Ala, Gln, Glu, Gly, His, Ile, Leu, Met, Ser, Thr, Trp, Tyr or Val, in particular to Gly, Ala, Ser, or Thr and preferably to Gly. Furthermore, Asn at position B3 may be modified to Lys. Further examples of insulin analogues are des(B30) human insulin, insulin analogues wherein PheB1 has been deleted; insulin analogues wherein the A-chain and/or the B-chain have an N-terminal extension and insulin analogues wherein the A-chain and/or the B-chain have a C-terminal extension. Thus one or two Arg may be added to position B1.

Also, precursors or intermediates for other proteins may be purified by the method of the invention. An example of such a precursor is an insulin precursor which comprises the amino acid sequence B(1-29)-AlaAlaLys-A(1-21) wherein A(1-21) is the A chain of human insulin and B(1-29) is the B chain of human insulin in which Thr(B30) is missing.

Human growth hormone analogues may be Ser-hGH or hGH-Leu-Ala. GLP1 analogues may be K34R-GLP-1(9-37) and GLP2 analogues may be $Gly^2$-GLP-2(1-33) or $Lys^{17}Arg^{30}$-GLP-2(1-33).

In the present context the three-letter or one-letter indications of the amino acids have been used in their conventional meaning as indicated in table 1. Unless indicated explicitly, the amino acids mentioned herein are L-amino acids. Further, the left and right ends of an amino acid sequence of a peptide are, respectively, the N- and C-termini unless otherwise specified.

TABLE 1

Abbreviations for amino acids:

| Amino acid | Three-letter code | One-letter code |
|---|---|---|
| Glycine | Gly | G |
| Proline | Pro | P |
| Alanine | Ala | A |
| Valine | Val | V |
| Leucine | Leu | L |
| Isoleucine | Ile | I |
| Methionine | Met | M |
| Cysteine | Cys | C |
| Phenylalanine | Phe | F |
| Tyrosine | Tyr | Y |
| Tryptophan | Trp | W |
| Histidine | His | H |
| Lysine | Lys | K |
| Arginine | Arg | R |
| Glutamine | Gln | Q |
| Asparagine | Asn | N |
| Glutamic Acid | Glu | E |
| Aspartic Acid | Asp | D |
| Serine | Ser | S |
| Threonine | Thr | T |

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

EXAMPLES

Example 1

Cloning and Expression of hGH in *E. coli* Fused to the Purification Tag SEQ ID NO:1 and Different Linkers 1. Cloning SEQ ID NO:1 is the 30S ribosomal protein S21 derived from sequenced genome of the thermophile *Bacillus stearothermophillus*. The molecular weight of the tag was calculated to 6.7 kDa and the pl of the tag was calculated to 11.3. When fused to human hGH the fusion protein(NNC20) including the linker with SEQ ID NO:6 will have a molecular weight of 29.9 kDa and a pl of 9.2.

The rpsU gene encoding the purification tag was codon optimized for expression in *E. coli*. The tag was assembled from 6 different primers covering the entire gene sequence by splicing by overlap extension (SOE). Two consecutive rounds of PCR were performed.

In the first reaction all 6 primers were allowed to assembly in a standard PCR reaction using 15 cycles and a lowered annealing temperature of 50° C. The PCR conditions were as follows using the Pyrobest polymerase system (Takara):

95° C.: 3 min. (denaturing)
94° C.: 45 sec (denaturing)
50° C.: 45 sec (annealing)
72° C.: 45 sec (extension)
15 cycles
72° C.: 10 min For the second PCR reaction a 1/50 dilution of the PCR product from the first reaction was used as template and the primers comprising the 5' and 3'-ends of the gene were used to amplify the full length tag. The PCR conditions for the 2. PCR reaction was the same as for the first, except that the annealing temperature was increased to 54° C. and the number of cycles to 25.

The terminal 5'-end forward primer matching the 5'-end of the rspU gene was designed with a NdeI restriction enzyme cleavage site and the terminal 3'-reverse primer comprised a SacII site. The NdeI and SacII site were chosen as they could be used as cloning sites for ligation of the purification tag sequence into a pET11a expression vector (Novagen) already comprising human growth hormone encoding sequence with a N-terminal ubiquitin tag and a linker containing a SacII site in front of the enterokinase cleavage site DDDDK (SEQ ID NO:10).

The second PCR product was purified from a clear band on an agarose gel and cleaved with NdeI and SacII restriction enzymes. The pET11a expression vector was also cleaved with NdeI and SacII. Ligation of the linarized vector with the RS21_BACST insert using T4-ligase yields a construct encoding the RS21_BACST tag linked to mature hGH with an intervening RRGGSDDDDK (SEQ ID NO:6) linker. The ligation product was transformed into *E. coli* JM109 on LB-ampicillin plates. Colonies on plates were propagated overnight and plasmids from these were isolated by standard mini prep methods and were evaluated for the presence of the purification tag insert by means restriction enzyme cleavage with NdeI and SacII. Plasmids with the correct cleavage pattern were DNA sequenced. Plasmids with the correct DNA sequence were transformed into *E. coli* expression strain BL21, which were plated on LB/ampicillin plates overnight, respectively.

Other pET11a expression vectors encoding variants of hGH fusion proteins with different linker regions were created. In general, this was accomplished by removal of the linker SEQ ID NO:6 regions with suitable restriction cleavage enzymes and ligation with double stranded oligos encoding the new linker region. The oligoes were obtained by annealing of two complementary oligoes encoding the new linker and which had cohesive ends compatible with those in the linearized vector. The following fusion hGH constructs were cloned:

| Product name | Tag | Linker |
|---|---|---|
| NNC20 | SEQ ID NO: 1 | SEQ ID NO: 6 |
| NNC20.1 | SEQ ID NO: 1 | SEQ ID NO: 7 |
| NNC20.2 | SEQ ID NO: 1 | SEQ ID NO: 8 |
| NNC20.3 | SEQ ID NO: 1 | SEQ ID NO: 9 |

2. Expression in *E. coli* BL21

*E. coli* BL21 cells transformed with plasmids encoding fusion constructs of hGH were grown to a OD600 of ~0.6 at 37° C. The temperature was then lowered to 25° C. for approximately 30 min, and 0.5 or 1 mM IPTG was added to the culture for 3 hours. Cells were then harvested by centrifugation. SDS-PAGE analysis could visualize that an hGH fusion protein of the correct size could be induced in *E. coli*. Comparison between the different constructs with showed differences in the amount of full length fusion protein that could be obtained after induction with IPTG. Thus NNC20.3 was expressed in a higher yield than observed for NNC20, NN20.1, NN20.2 and NN20.2.

NNC20 and NNC20.3 were >80% soluble when induced for 3 hours at 25° C. and had an Mw of ~30 kDa as calculated from the amino acid sequence.

3. Purification of NNC20

Initially, a binding assay using pellets dissolved in different buffers with different salt concentrations and pH showed that the fusion protein efficiently bind to SP sepharose FF matrix (Amersham Pharmacia) up to a pH of 9 and at salt concentration of up to 0.3 M NaCl. This indicates that the SEQ ID NO:1-hGH protein can be purified at conditions where only very few other proteins should be able to bind the matrix.

Pellet from 80 ml culture of *E. coli* BL21 expressing NNC20 was sonicated in 25 mM sodium phosphate, 5 mM EDTA pH 8 and cell debris was removed by centrifugation. After sonication NaCl was added to a final concentration of 0.3 M to decrease the ability of *E. coli* contaminants to bind to the cation exchange matrix and the application was sterile filtrated. Purification was done on an AKTA explorer (Amersham Pharmacia) with a flow rate of 0.5 ml/min. The following buffers were used:

Buffer A: 25 mM sodium phosphate, 5 mM EDTA, pH8, 0.3M NaCl

Buffer B: 25 mM sodium phosphate, 5 mM EDTA, pH8, 1 M NaCl,

Buffer C: 2M NaCl

The prepacked SP FF (HR5/5) column (Amersham Pharmacia) was equilibrated with buffer A for 5 column volumes (CV). The application containing NNC20 was loaded on the column and unbound sample was washed out with buffer A for 20 CV. A gradient from 0-50% buffer B was used for 20 CV. Finally an isocratic step using buffer C for 10 CV was used to elute the target protein from the column.

Figure 2:
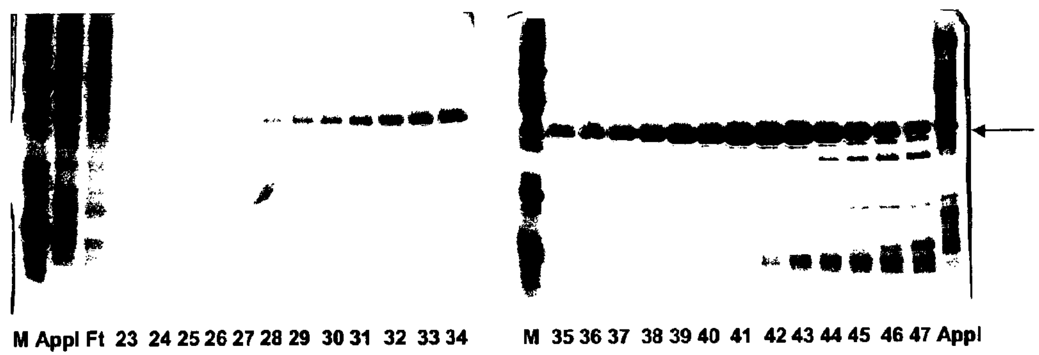
FIG. 2 discloses two non-reducing SDS-PAGE gel images of fractions 23-47 collected from the main NNC20 peak from purification on AKTA explorer described in example 1, where M is Protein marker, Appl. is NNC20 Application and Ft is Flow through. Arrow indicates position of eluted fusion protein.

Fractions containing the eluted fusion protein were collected and the purity of the fusion protein present in the NNC20 main peak of the chromatogram was evaluated by SDS-PAGE image analysis. Coomasie stained SDS PAGE gels of the fraction covering the NNC20 main peak estimated the purity of the protein to be >90% FIG. 2 shows the fractions collected from the NNC20 main peak, which contains the fusion protein run on a SDS-PAGE gel at non-reducing conditions.

4. Purification of NNC20.3

NNC20.3 was expressed in *E. coli* BL21 as described for pNNC20 except that only 0.5 mM IPTG used to induce the fusion protein. Pellet from 40 ml of culture was dissolved to an OD600 of 5 in 25 mM sodium phosphate buffer pH 7 and cell debris was removed by centrifugation. The resulting supernatant was sterile filtrated and purified on the AKTA explorer at a flow rate of 0.5 ml/min using the following buffers:

Buffer A: 25 mM sodium phosphate pH 7

Buffer B: 25 mM sodium phosphate pH 7 and 1 M NaCl

Figure 3A:
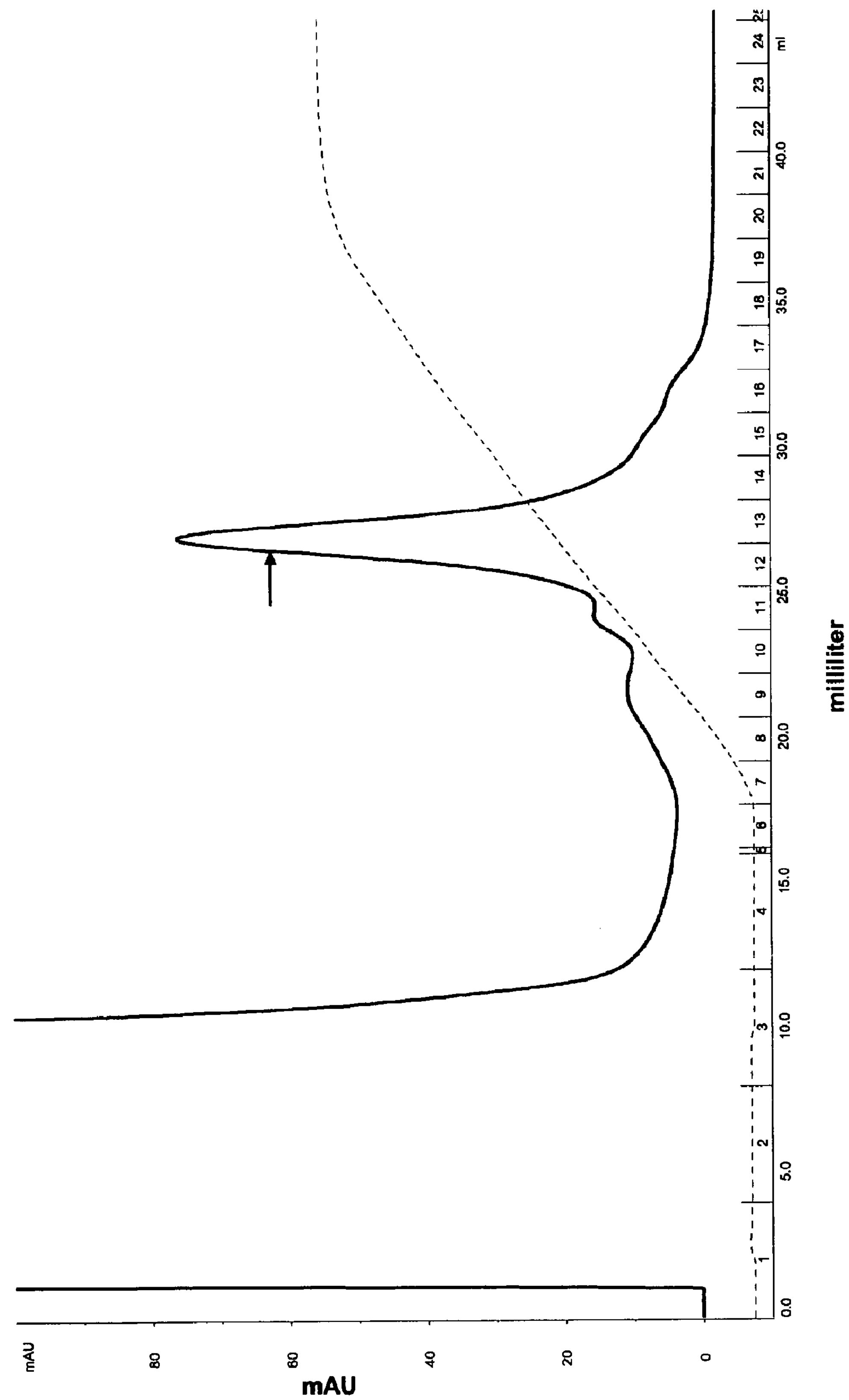
FIG. 3A shows the purification described in example 1 and FIG. 3B shows the chromatogram of an hGH fusion protein purification described in example 2. Arrows point at the main peak containing the eluted fusion protein. Stippled curves indicate the conductivity (milli Siemens/cm) measured during the gradient formed by adding NaCl. Solid lines indicate the UV280 measured during the purification.

A 1 ml column packed manually with SP FF matrix (Amersham Pharmacia) was equilibrated with buffer A for 5 column volumes (CV). The application containing NNC20.3 was loaded on the column and unbound sample was washed out with buffer A for 7 CV. A gradient from 0-100% buffer B was used for 20 CV during which the fusion protein was eluted at a NaCl concentration of approximately 0.5 M. The purity of the fusion protein present in the main peak was estimated to be approximately 90% using the ImageJ analysis software (Rasband, W. S., ImageJ, U.S. National Institutes of Health, Bethesda, Md., USA, http://rsb.info.nih.gov/ij/, 1997-2005). FIG. 3A shows a chromatogram showing the elution of NNC20.3 at approximately half maximal conductivity.

Fraction 13 and 14 representing a volume of ~3 ml were pooled and digested with 0.01 U/ml of recombinant bovine enterokinase light chain for 6 hours at room temperature. SDS PAGE showed that the ~30 kDa fusion protein band almost disappeared and a band of ~22 kDa corresponding to mature hGH without the purification tag appeared as well as a band of ~6 kDa representing the released purification tag. The digested sample was then diluted ~5 times in 25 mM sodium phosphate pH 7, 10 mM PMSF buffer (PMSF was added to minimize previously described unspecific EK cleavage in the hGH sequence). This was done in order to lower the salt concentration, so that the highly basic protein co-eluting with the fusion protein in the first run as well as the purification tag released by EK would efficiently bind the cation exchange column in the second run. The diluted sample was run using the SP FF column with same parameters as described above. The flow through was collected and up-concentrated using a Vivaspin 15 ultrafiltration column (Vivascience) a 3000 rpm until the volume was reduced ~5 times. SDS-PAGE analysis of the up-concentrated flow through sample showed that it contained essentially pure mature hGH, only contaminated with small amounts of hGH fragments coming from unspecific cleavage due to EK. The released tag, remaining uncleaved fusion protein and contaminants co-eluting with NNC20.3 in the first step is thus retained on the cation-exchange column in the second purification step.

Other data prove that the fusion proteins can be expressed without significant degradation of the purification tags measured as indicated by Coomasie stained PAGE gels or by Western Blotting. Also upon peptide mass mapping using MALDI mass spectrometry of SEQ ID NO:1-hGH constructs only very few peptides were found after cleavage with trypsin, altogether indicating high resistance of the tag towards trypsin-like proteases. MALDI analysis of disulphide bridges in SEQ ID NO:1-hGH(NNC20.3) also indicated that the SEQ ID NO:1-tag did not interfere with the establishment of the correct disulphide bridges in the hGH target protein.

In the binding assay evaluating the binding of NNC20 expressed in *E. coli*, to SP sepharose fast flow matrix at different salt concentrations and buffers it was observed that the fusion protein efficiently binds to SP sepharose up to pH 9 and at salt concentration up to 0.3 M NaCl.

Example 2

Cloning and Expression of Fusion Constructs of SEQ ID NO:2, SEQ ID NO:15 and hGH in *E. Coli*

SEQ ID NO:2 is the 30S ribosomal protein L39 derived from the sequenced genome of the thermophile *Archaeoglobus fulgidus*

The molecular weight of the purification tag was calculated to 5.9 kDa and the pl of the tag was calculated to 12.5. When fused to human hGH the fusion protein will have a molecular weight of 29.2 kDa and a pl of 9.5. The rpl39e gene encoding the tag was codon optimized for expression in *E. coli*. The tag was assembled from 6 different primers covering the entire gene sequence by splicing by overlap extension (SOE) PCR. Two consecutive rounds of PCR were used essentially as described for pNNC20 in example 1. The 5-end primer matching the 5'-end of the rpl39e gene was designed with a NdeI restriction enzyme cleavage site and the terminal reverse primer comprised the 3'-end of the rpI39e gene and overhang comprising a NheI site. PCR product was sub-cloned into the pCR2.1 TOPO vector according to the manufactures instructions (Invitrogen) and the sequence was verified by DNA sequencing. The purification tag part was cut out of the TOPO vector and ligated together with a purified pNNC20.3 vector linearized with NdeI and NheI using the Rapid ligation Kit (Roche). The ligation product was transformed into *E. coli* TOP10 for amplification of the new plasmid overnight by plating on LB/ampecillin plates. Plasmids from overnight colonies were obtained and were evaluated by means restriction enzyme cleavage and DNA sequencing. A clone comprising the correct fusion product consisting of SEQ ID NO:2, SEQ ID NO:15 and hGH was isolated, transformed into *E. coli* expression strain BL21 and expressed at 25° C. for 3 hours using 0.5 mM IPTG as described in Example 1. SDS-PAGE showed that the construct yielded a fusion protein of the correct size of ~30 kDa, which was approximately 80% soluble.

Pellets of the expressed fusion product of SEQ ID NO:2, SEQ ID NO:15 and hGH from 40 ml culture was sonicated in 20 mM $KPO_4$ pH 7, 0.1% Triton X-100 and cell debris was removed by centrifugation. The resulting supernatant was sterile filtrated and purified using the AKTA explorer at a flow rate of 1 ml/min with the following buffers:

Buffer A: 20 mM potassium phosphate pH 7

Buffer B: 20 mM potassium phosphate pH 7 and 1 M NaCl

Figure 3B:
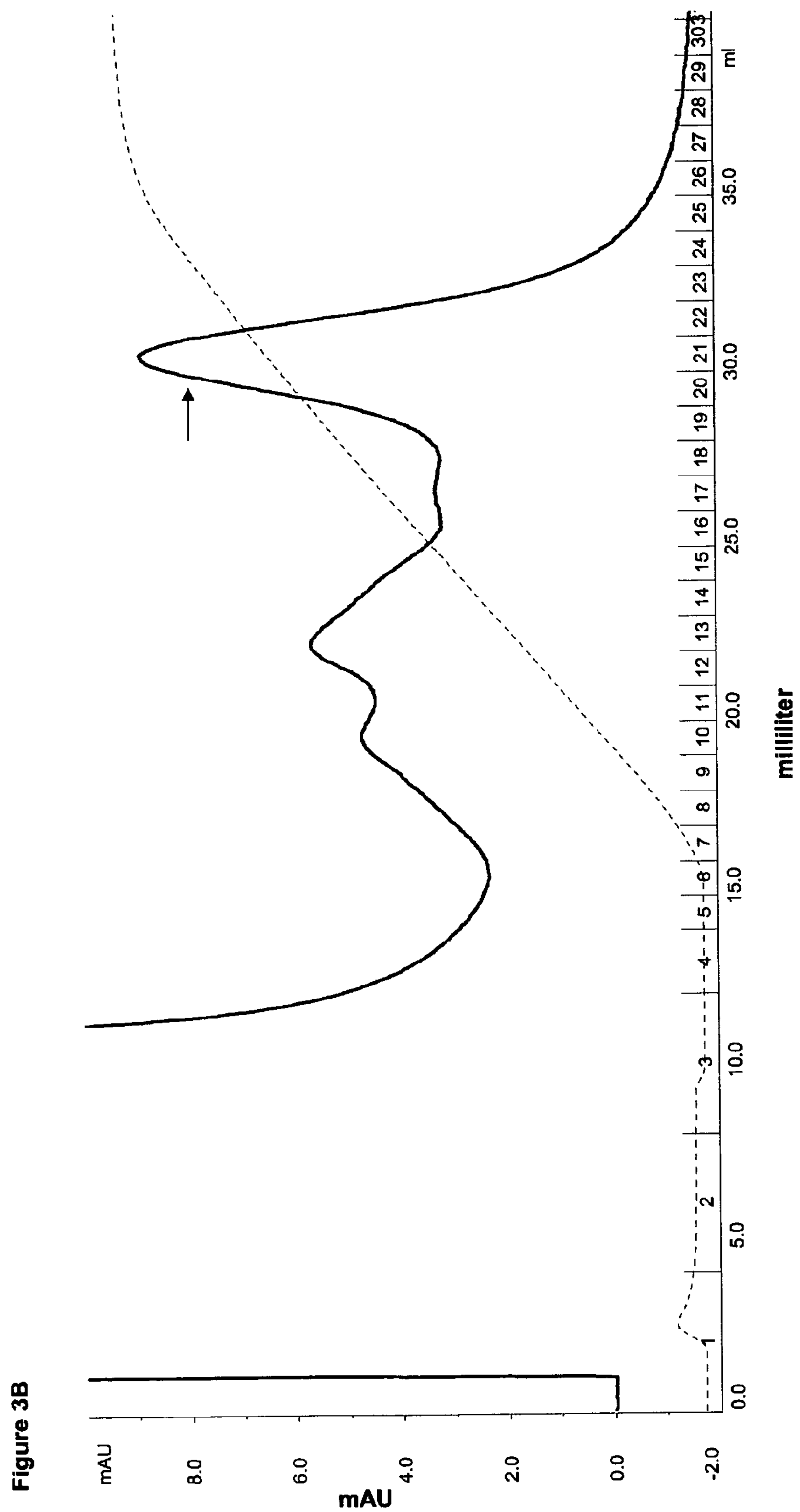

A 1 ml column packed manually with SP FF matrix (Amersham Pharmacia) was equilibrated with buffer A for 5 column volumes (CV). The application containing the tagged hGH was loaded on the column and unbound sample was washed out with buffer A for 5 CV. A gradient from 0-100% buffer B was used for 20 CV during which the target protein was eluted. The purity of the target protein present in the main peak was estimated to be approximately 90%. FIG. 3B is a chromatogram showing the elution of the fusion product of SEQ ID NO:2, SEQ ID NO:15 and hGH at approximately 0.8 M NaCl.

Example 3

Cloning of hGH Leu-Ala Variants

The C-terminal of hGH in the fusion protein described in Example 1 (NNC20.3) was extended with Leu-Ala. In short, PCR amplification was carried out with a forward primer spanning a Bsu36I site 300 bp from the stop codon in hGH encoding sequence of pNNC20.3. The reverse primer had two extra codons encoding Leu-Ala before the stop codon terminating the mature hGH sequence and a 5'-end BamHI cloning site. The template used was pNNC20.3. This PCR product was purified using the GFX Purification Kit (Amersham Pharmacia) and cloned into the pCRIITOPO vector (Invitrogen) and sequenced. Insert with correct sequence was excised with Bsu36I and BamHI and ligated into pNNC20.3 cleaved with Bsu36I and BamHI. This yields a SEQ ID NO:1-SEQ ID NO:9-hGH-Leu-Ala construct pACSH74.

A number of purification tags (SEQ ID NO: 20 to 42) have been tested for expression levels, solubility and purification potential. These tags are derived from genes encoding 23 different highly basic ribosomal proteins were PCR amplified from genomic DNA of *Thermotoga maritima* (obtained from American Type Culture Collection, ATCC 43589).

In short, an NdeI cloning site was included in the forward primer immediately upstream of the start codon of the ribosomal protein encoding sequence. An XhoI cloning site was included to the reverse primer after the codon encoding the last aa of the ribosomal protein encoding sequence. The PCR products were purified from agarose gels and cloned into the pCRII TOPO vector. NdeI/XhoI inserts with correct sequence were exicised from TOPO clones ligated into an pACSH74, thus replacing the SEQ ID NO:1. All constructs have the linker SSSSTLAAPFDDDDK (SEQ ID NO:9) between the N-terminal tag and the start phenylalanine of the hGH-Leu-Ala sequence.

The following hGH-Leu-Ala fusion proteins were cloned:

| Product name | Tag | Linker |
|---|---|---|
| ACSH74 | SEQ ID NO: 1 | SEQ ID NO: 9 |
| ACSH118 | SEQ ID NO: 20 | SEQ ID NO: 9 |
| ACSH119 | SEQ ID NO: 21 | SEQ ID NO: 9 |
| ACSH120 | SEQ ID NO: 22 | SEQ ID NO: 9 |
| ACSH121 | SEQ ID NO: 23 | SEQ ID NO: 9 |

-continued

| Product name | Tag | Linker |
|---|---|---|
| ACSH122 | SEQ ID NO: 24 | SEQ ID NO: 9 |
| ACSH123 | SEQ ID NO: 25 | SEQ ID NO: 9 |
| ACSH124 | SEQ ID NO: 26 | SEQ ID NO: 9 |
| ACSH125 | SEQ ID NO: 27 | SEQ ID NO: 9 |
| ACSH126 | SEQ ID NO: 28 | SEQ ID NO: 9 |
| ACSH127 | SEQ ID NO: 29 | SEQ ID NO: 9 |
| ACSH128 | SEQ ID NO: 30 | SEQ ID NO: 9 |
| ACSH129 | SEQ ID NO: 31 | SEQ ID NO: 9 |
| ACSH130 | SEQ ID NO: 32 | SEQ ID NO: 9 |
| ACSH131 | SEQ ID NO: 33 | SEQ ID NO: 9 |
| ACSH132 | SEQ ID NO: 34 | SEQ ID NO: 9 |
| ACSH133 | SEQ ID NO: 35 | SEQ ID NO: 9 |
| ACSH134 | SEQ ID NO: 36 | SEQ ID NO: 9 |
| ACSH135 | SEQ ID NO: 37 | SEQ ID NO: 9 |
| ACSH136 | SEQ ID NO: 38 | SEQ ID NO: 9 |
| ACSH137 | SEQ ID NO: 39 | SEQ ID NO: 9 |
| ACSH140 | SEQ ID NO: 40 | SEQ ID NO: 9 |
| ACSH142 | SEQ ID NO: 41 | SEQ ID NO: 9 |
| ACSH143 | SEQ ID NO: 42 | SEQ ID NO: 9 |

Expression of hGH-Leu-Ala Constructs in *E. coli* and Binding Assay:

23 hGH-Leu-Ala constructs with purification tags amplified from *Thermotoga maritima* were transformed into Rosetta (DE3) strain. Cells were grown to a OD600 of ~0.4-0.6 at 37° C. Then the temperature was lowered to 30° C. for approximately 30 min and 0.5 IPTG was added to the culture for 3 hours. All constructs gave a clear protein band of the expected size. Expression levels differed somewhat between constructs. They all showed a solubility of between about 50% to more than 80% after sonication in 10 mM phosphate buffer.

Six candidates were tested for their affinity for binding SP FF on small columns loaded with 0.75 ml SP FF matrix. The Method used was as follows:

Buffer A: 25 mM $Na_2HPO_4NaH_2PO_4$ pH 7

Buffer B1: 25 mM $Na_2HPO_4NaH_2PO_4$ pH 7 0.5 M NaCl

Buffer B2: 25 mM $Na_2HPO_4NaH_2PO_4$ pH 7 1 M NaCl

1) Wash columns with 5 ml water, 2 ml buffer A, 3 ml buffer B2
2) Equilibrate in 6 ml buffer A
3) Load cell supernatants and collect flow through (FT)
4) Wash with 3 ml of buffer A and collect FT
5) Elute with 2 ml buffer B1 and collect FT
6) Elute with 2 ml buffer B2 and collect FT ACSH122 and ACSH200 were almost completely eluted with 0.5 M NaCl and ACSH198, ACSH199 and ACSH74 were eluted with both 0.5 and 1 M NaCl, indicating stronger interaction with the column. No fusion protein at all was observed in the flow through for ACSH74, whereas the rest showed differences in the binding efficiency.

AKTA Purification of ACSH74, ACSH130 and ACSH131:

Purification of ACSH 74

ACSH74 was expressed in BL21 (DE3) and purified as described for NN20.3 in example 1. The results were almost identical with those obtained for NN20.3 indicating that the Leu-Ala extension in the C-terminal did not influence the binding of the tag to the SP FF Purification of ACSH130 and ACSH131:

Pellets from 40 ml of culture were sonicated in 25 mM $NaPO_4$ pH 7 as described in example 1. Purification was done on an AKTA explorer (Amersham Pharmacia) with a flow rate of 5 ml/min using a HiTrap5 ml SP FF column (Amersham Pharmacia) and the following buffers:

Buffer A: 25 mM sodium phosphate, pH 7

Buffer B: 25 mM sodium phosphate, pH 7+1M NaCl

The column was equilibrated with buffer A for 5 column volumes (CV). The application containing ACSH131 or ACSH130 was loaded on the column and unbound sample was washed out with buffer A for 7 CV. A gradient from 0-100% buffer B was used for 20 CV. ACSH131 and ACSH130 was eluted from the column with approximately 50% Buffer B(0.5 NaCl). For both ACSH131 and ACS130 binding to SP FF was less efficient than observed for NN20, NN20.3 and ACSH74, but the purity was at a similar high level.

Example 4

Cloning of Insulin Antagonist S661 Fusion Proteins

S661 is a insulin receptor antagonist The peptide comprises one disulphide bridge and has the following sequence:

```
SEQ ID NO: 43:
GSLDESFYDWFERQLGGGSGGSSLEEEWAQIQCEVWGRGCPSY
```

The nucleotide sequence of S661 sequence was codon optimized for optimal expression in *E. coli*. A XhoI site and BamHI cloning site was included in the 5'end and 3'-end of the S661 sequence to enable easy cloning into existing hGH-Leu-Ala constructs (Example 3). The S661 sequence was synthesized by Splicing by overlap extension PCR as described previously. In short, 3 forward primers and 3 reverse primers of ~50 bp in length were designed cover the S661 sequence with XhoI/BamHI cloning sites with overlaps of approx 20 bp. The linker encoding SSSSDDDDK (SEQ ID NO:16 was added between the purification tags and S661.

Two rounds of PCR was performed as using the Phusion PCR Kit (Finnzymes) at conditions recommended by the manufacturer.

The first PCR reaction had the following conditions:

98° C. 30 sec,

98° C. 10 sec (denaturation)

50° C. 30 sec (annealing)

72° C. 15 sec (elongation)

10 cycles

72° C. 5 min

First PCR product was excised from 2% agarose gels and purified by GFX kit (GE Health care), diluted 1/50 and use as template for the last PCR reaction. The second PCR reaction was performed with the most terminal two primers comprising the XhoI and BamHI cloning sites using the same conditions as for the first reaction except that 55° C. was used as annealing temperature and 15 cycles was used. A band of the expected size was excised from 2% agarose gels, purified by GFX kit (GE Health Care) and ligated into pCRIITOPO vector (Invitrogen) as described by the manufacturer. A clone with correct sequence was isolated and the S661 insert was released with XhoI and BamHI and ligated into the vector part of different hGH-Leu-Ala constructs from which hGH-Leu-Ala had been excised with XhoI/BamHI. This yielded the following constructs with different purification tags N-terminal linked to the S661 sequence with different linkers:

| Product name | Tag | Linker |
|---|---|---|
| ACSH197 | SEQ ID NO: 24 | SEQ ID NO: 16 |
| ACSH198 | SEQ ID NO: 31 | SEQ ID NO: 16 |
| ACSH199 | SEQ ID NO: 32 | SEQ ID NO: 16 |
| ACSH200 | SEQ ID NO: 33 | SEQ ID NO: 16 |

Expression of ACSH197-ACSH200 pACSH197-ACSH201 was transformed into Rosetta (DE3)(Novagen), which were cultivated in the presence of Ampecillin and Chloramphinicol as described by the manufacturer. Cells were grown to a OD600 of ~0.4-0.6 at 37° C. The temperature was then lowered to 30° C. for approximately 30 min. Protein synthesis was then induced with 0.5 mM IPTG for 3 hours at 30° C. Cell with induced protein were harvested by centrifugation. SDS evaluation showed that all constructs expressed a protein of the expected size, with minor differences in expression levels and solubility.

Purification of ACSH200

Cells from 40 ml culture of *E. coli* Rosetta(DE3) from a 3 hour expression of ACSH200 in 200 ml medium (final OD 600=1.6) at 30° C. was sonicated in 10 ml 25 mM sodium phosphate pH 8.5, cell debris was removed by centrifugation and the application was sterile filtrated and diluted to 20 ml with 25 mM sodium phosphate buffer. The solubility was >80% for this fusion protein. Purification was done on an AKTA explorer (Amersham Pharmacia) with a HiTrap SP-FF, 5 ml column with a 5 ml/min flow rate. The following buffers were used:

Buffer A: 50 mM sodium phosphate, pH 8.5

Buffer B: 50 mM sodium phosphate, pH 8.5+1 M NaCl

A 5 ml SP FF (HR5/5) column (Amersham Pharmacia) was equilibrated with buffer A for 5 column volumes (CV). The application containing ACSH200 was loaded on the column and unbound sample was washed out with buffer A for 5 CV. A gradient from 0-100% buffer B was used for 20 CV.ACSH200 was eluted at approximately 30% buffer B (0.3 M NaCl) (FIG. 3A). Fractions containing the eluted fusion protein were collected and the purity of the fusion protein present in the main peak of the chromatogram was evaluated by SDS-PAGE (FIG. 3B) and software analysis. No protein was detected in the flow through indicating that all protein did bind the SP FF column. Coomasie stained SDS PAGE gels of the fraction covering the ACSH200 main peak estimated the purity of the protein to be ~90%. A similar purification was performed at pH 7, which gave the same mAU signal (but somewhat less purity) indicating that recovery of the purified protein is not affected by pH 8.5 of the buffer. This is advantages as less contaminant protein can bind the column at pH 8.5.

LC-MS Analysis of Fraction 25 from Purification of ACSH200

Fraction 25 from purification was diluted 1:1 with sodium phosphate buffer and 20 uL was analyzed on a LC-MSD_TOF (Agilent technologies) instrument using an analytical Poroshell 300SB-C8, Micro Bore 1.0×75 mm, 5 micron (Agilent Technologies) column at standard HPLC conditions with a flow of 0.3 ml/min and a column temperature of 70° C.: A gradient elution was formed in a 20 min. run using 8.8 mM ammonium formate in 0.1% formic acid water (Buffer A) and Acetonitrile (Buffer B) as follows:

| Time(min) | % Buffer B |
|---|---|
| 0 | 22 |
| 3 | 22 |
| 15 | 75 |
| 15.1 | 90 |
| 20 | 90 |

MS settings were as recommended by the manufacturer

Figure 4A:
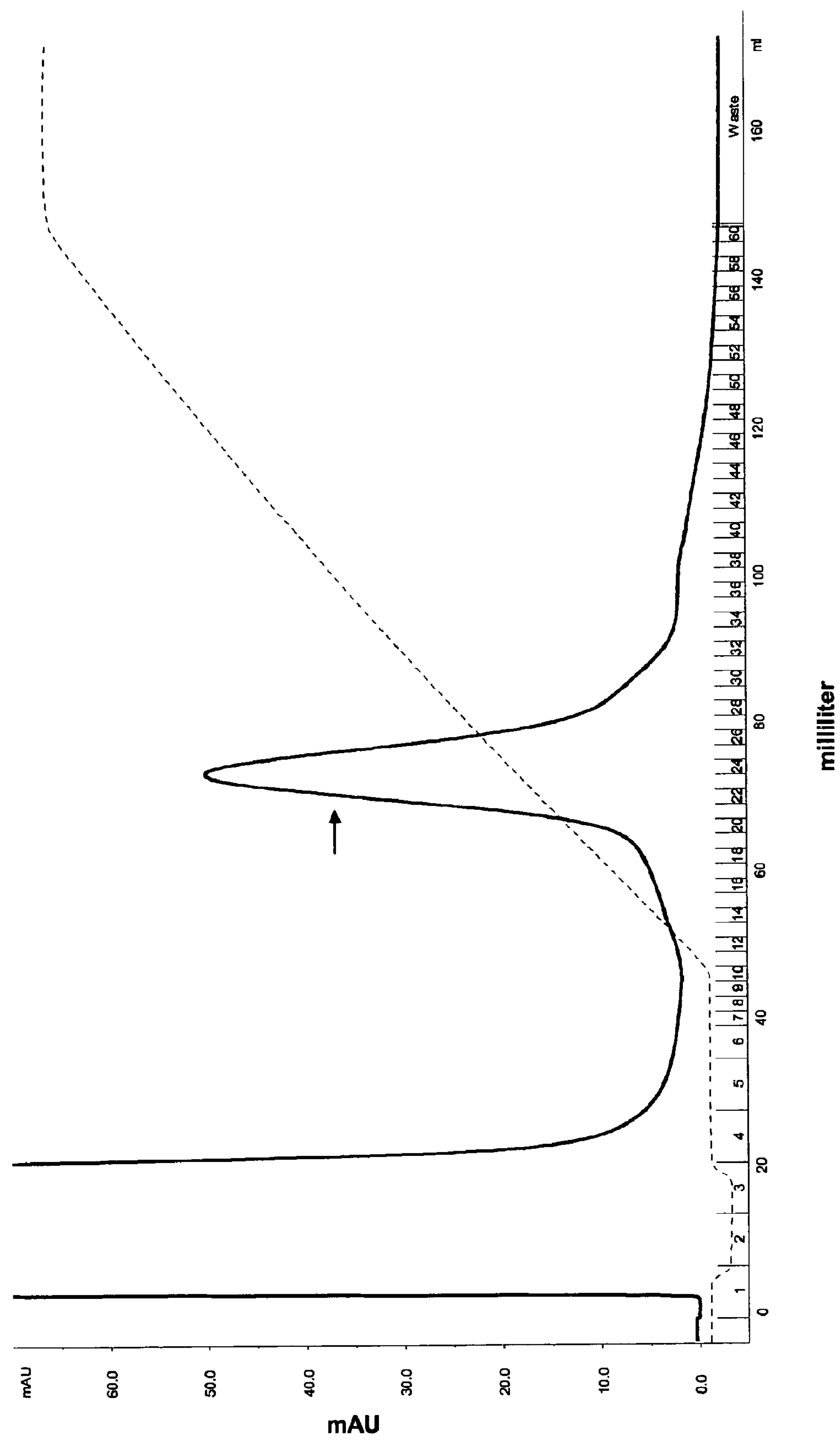
FIG. 4 discloses the chromatogram from purification of ACSH200 described in example 4 (4A), the corresponding SDS PAGE gel of the collected fractions (4B) (arrows point at eluted ACSH200 fusion protein) and the extracted deconvoluted MS spectrum from analysis of fraction 25 (4C) showing the mass of the intact ACSH200 fusion protein described in example 4.
Figure 4B:
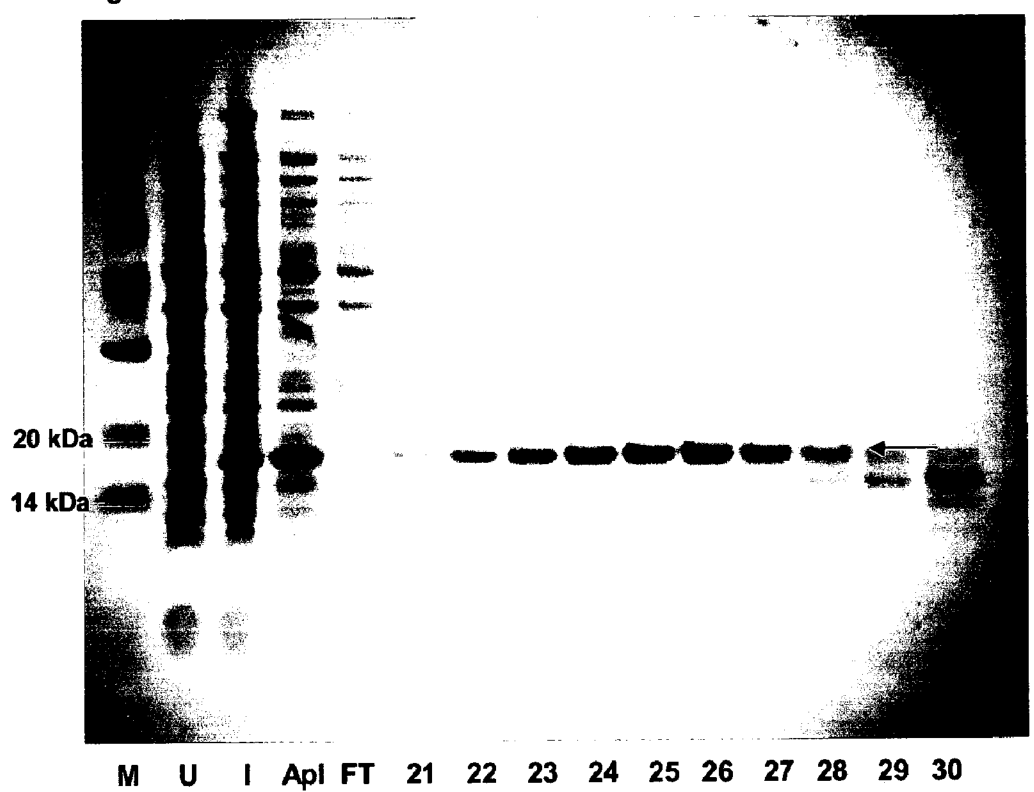
Figure 4C:
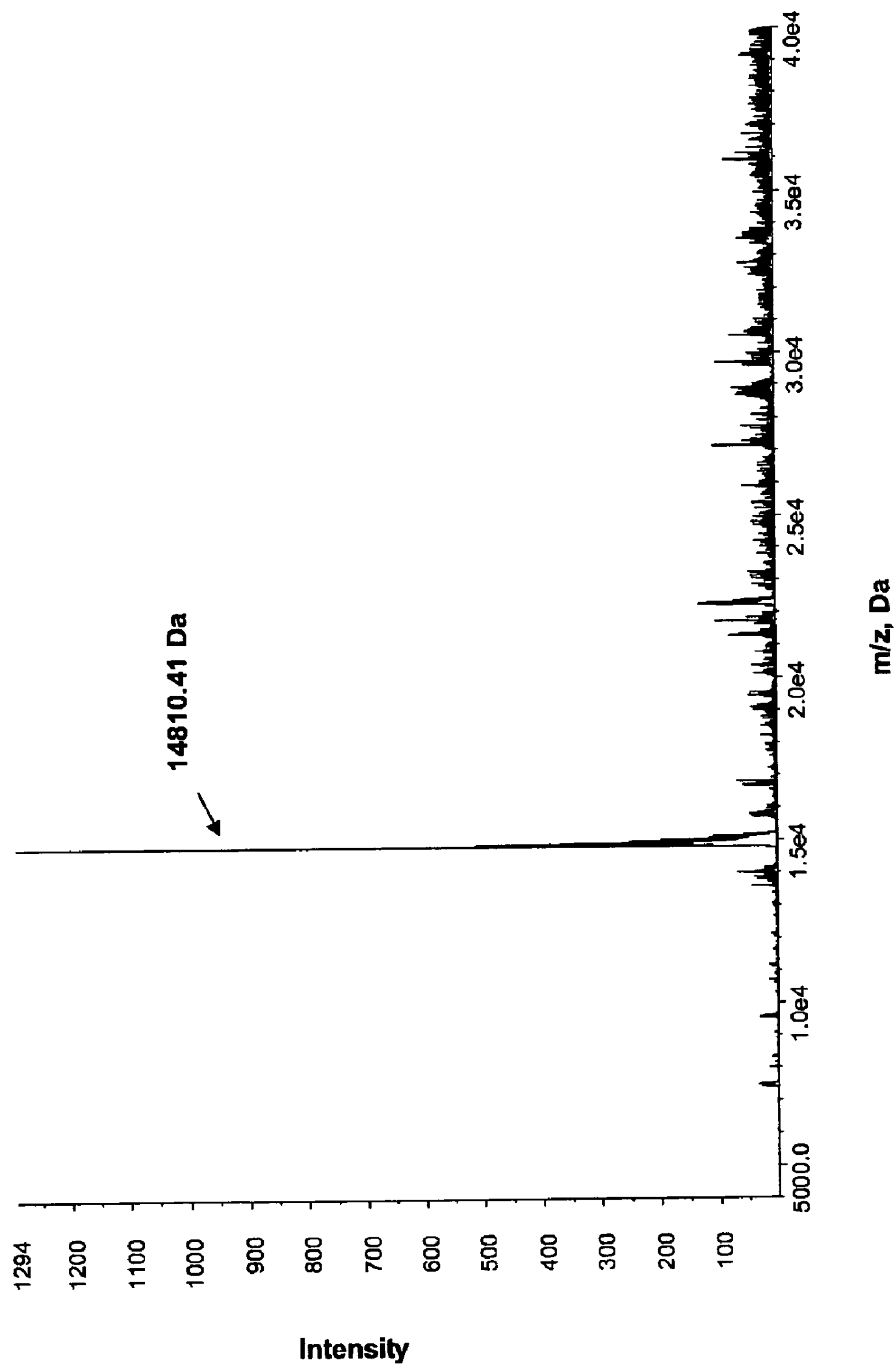

The TIC (total ion count) chromatogram obtained by LC-MS analysis predominantly showed one peak. The extracted deconvoluted spectrum of this peak showed a peak with the mass of 14810.41 Da very close to the predicted mass of 14810.45 Da of ACSH200 without the N-terminal methionine (which is removed by *E. coli* methionine amino peptidase) (FIG. 4C). The molecular mass of the fusion protein changed with ~2 Da upon 1 hour treatment with 50 mM DTT. Altogether this suggests that the disulphide bridge is correctly established in the protein, which shows that the RL27_THEMA (SEQ ID NO:33) tag does not interfere with correct establishment of the disulphide bridge.

Purification of ACSH199 and ACSH198

Purification of ACSH199 and ACSH198 was performed as described in for ACSH200.

ACSH199 and ACSH198 were eluted at approximately 50% buffer B (0.5 M NaCl), and showed less efficient binding to the column as protein was observed in the flowthrough. However, for both constructs the purity of fusion proteins in eluted fractions was comparable with that of ACSH200

Example 5

Thermoprecipitation of *E. coli* Contaminants

With ACSH200 as model protein it was investigated whether *E. coli* contaminants could be heat-precipitated at high temperatures, while the fusion protein due to the thermostability of the tag could be retained in solution.

Figure 5:
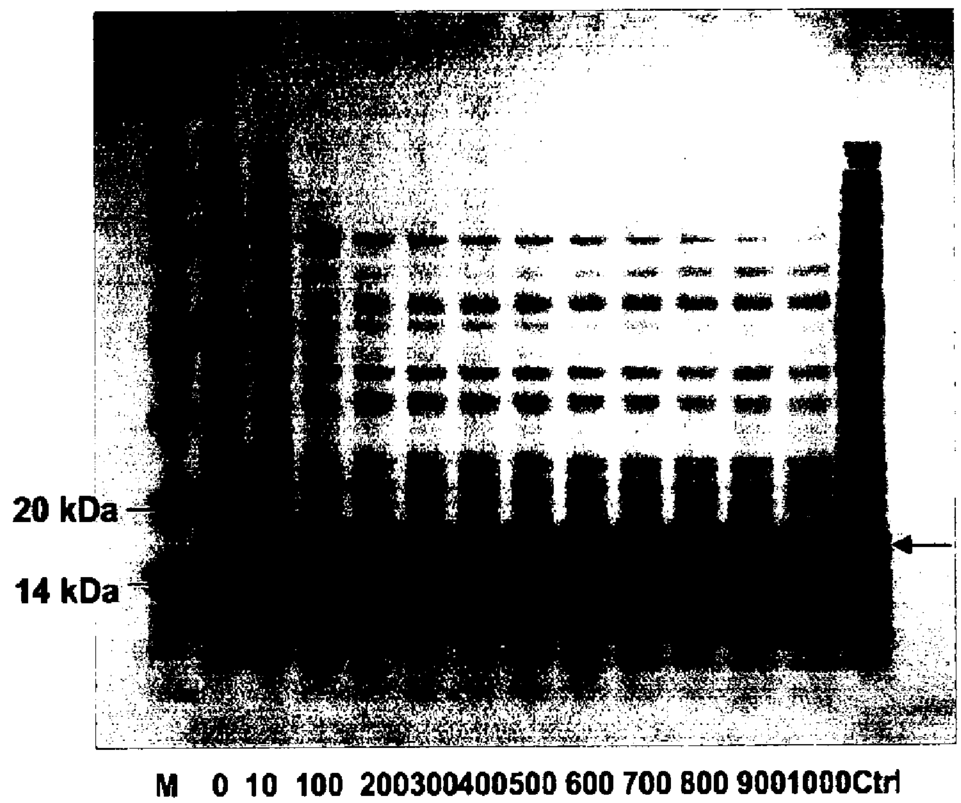
FIG. 5 discloses the SDS PAGE gel of supernatants with different NaCl concentration that were heat treated in a pre-column purification step as described in Example 5 where M is Protein marker. Arrow points at ACSH200 fusion protein. M: marker, 0-1000 mM NaCl added to the samples, Ctrl is a non heated control.

ACSH200 was expressed as described in Example 4. Pellets were dissolved in 25 mM sodium phosphate pH 7 and sonicated as described above. From 10 mM-1 M NaCl was added to the supernatant. The samples were heated for 70° C. for 30 min and immediately cooled on ice for 10 min. Samples were then centrifuged for 10 min. at 15.000 G and the supernatants were compared to a non-heated control using SDS PAGE. Significant amounts of especially high abundant *E. coli* contaminants could be removed with increasing NaCl conc. (FIG. 5). The heat precipitation did not affect the recovery of the target protein compared to the non-heated control indicating that the claimed purification tags do facilitate a precolumn purification step with thermo precipitation. Same efficiency of precipitation was obtained with this strategy using pH 8.5 in the buffer, indicating that the high pH can be combined with thermo precipitation, thus improving the starting material for cation exchange purification.

Example 6

Cloning of Human Amylin Fused to Purification Tags

Human amylin is a small peptide hormone comprising 37 aa:

```
SEQ ID NO: 44:
KCNTATCATQRLANFLVHSSNNFGAILSSTNVGSNTY
```

The nucleotide sequence of the human amylin sequence was codon optimized for optimal expression in *E. coli*. The coding sequence was generated by SOE PCR using 6 primers of ~50 bp in length with ~20 bp overlaps covering the entire human amylin sequence. The same general methodology and cloning sites (XhoI/BamHI) were used as described for S661 in Example 4. The following constructs were cloned:

| Product name | Tag | Linker |
|---|---|---|
| ACSH202 | SEQ ID NO: 24 | SEQ ID NO: 16 |
| ACSH203 | SEQ ID NO: 31 | SEQ ID NO: 16 |
| ACSH204 | SEQ ID NO: 32 | SEQ ID NO: 16 |
| ACSH205 | SEQ ID NO: 33 | SEQ ID NO: 16 |

Expression of ACSH202-205:

Expression was carried out as described for S661 constructs in Example 4. Protein bands of correct size were obtained for all constructs. Double bands were observed for ACSH202, ACSH203 and LC-MS analysis indicated cleavage by unknown *E. coli* proteases in the amylin sequence.

Figure 6A:
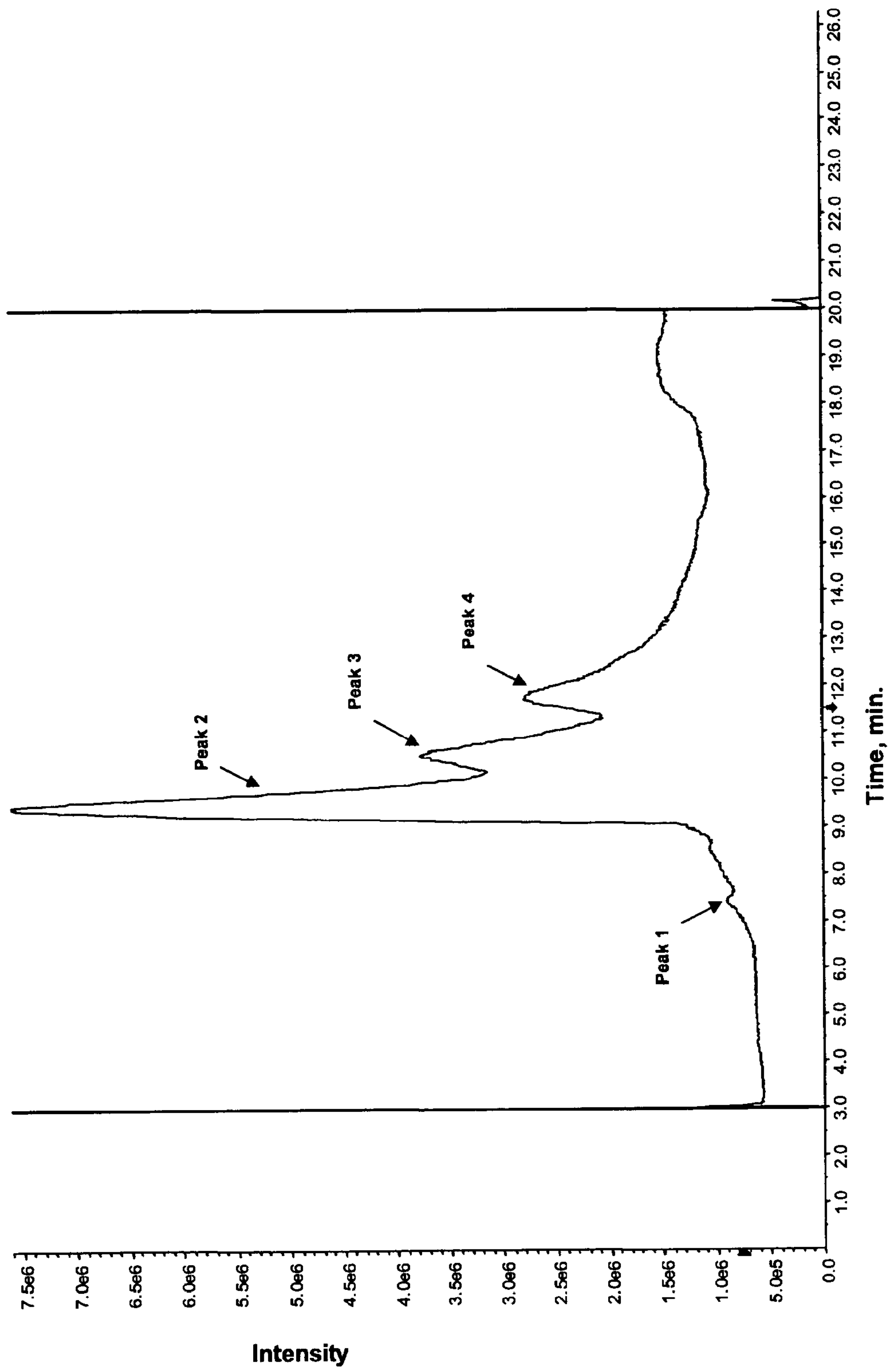
FIG. 6A discloses TIC chromatogram of enzymatic cleavage of pACSH204 showing total ions eluted from a Poroshell SB300 C8 (Agilent Technologies) column, Peak 1: Human Amylin, Peak 2: Purification tag released with EK, Peak 3: intact fusion protein, Peak 4: fragment due to unknown *E. coli* protease cleaving after 6 amino acid residues in Amylin FIG. 6B discloses extracted spectrum of Peak 1 comprising the released human Amylin peptide FIG. 6C discloses extracted and deconvoluted spectrum of Peak 2 comprising the released purification tag and FIG. 6 D discloses: extracted and deconvoluted spectrum of Peak 4 comprising the intact uncleaved ACSH204
Figure 6B:
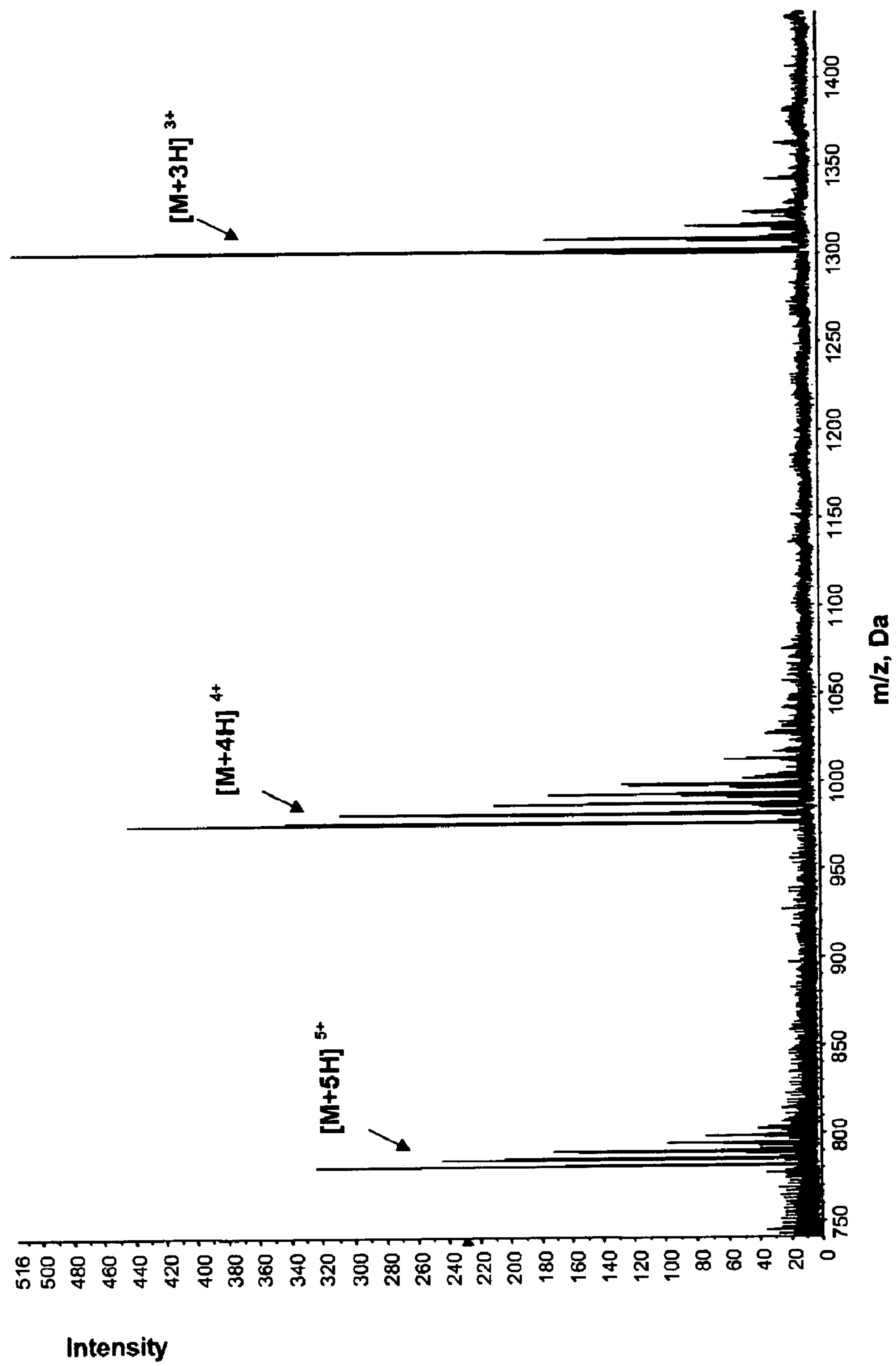
FIG. 6 discloses an LC-MS analysis of purified and EK digested ACSH204 fusion protein.

Purification of ACSH204 and Enterokinase Digestion of ACSH204:

Purification of ACSH204 was performed as described above using a buffer A and buffer B as described in example 4, but at pH 7. Fractions were collected and analysed. To evaluate whether EK can release human Amylin from the purification tag, 2 ml of the purest fraction of RL23_AMY representing the major peak was upconc. in Vivaspin 2, CTA 5000 Da MWCO (Vivascience, Satorius) to 1 ml and diluted 1:1 in 500 mM Tris HCl pH 7, 10 mM CaCl2. 0.003 U/uL EK was added to 400 uL reaction volume and incubated for 1 h at 37° C. The sample was analyzed with LC-MS as briefly described in Example 4 and the TIC chromatogram showed four distinct peaks (FIG. 6A). Extracted spectra of peak 1 showed the mass of human Amylin in 3 (1309.56×3-22 Da(Na adduct)−$3H^+$=3903.7, 4 (982.42 Da×4-22 Da(Na adduct)−$4H^+$=3903.7) or 5 charge states (781.74 Da×5-$5H^+$)=3903.7 (FIG. 6*b*). The mass of 3903.7 Da closely matched the theoretical average isotopic mass of human amylin with an intact disulphide bridge: 3904.3 Da.

Figure 6C:
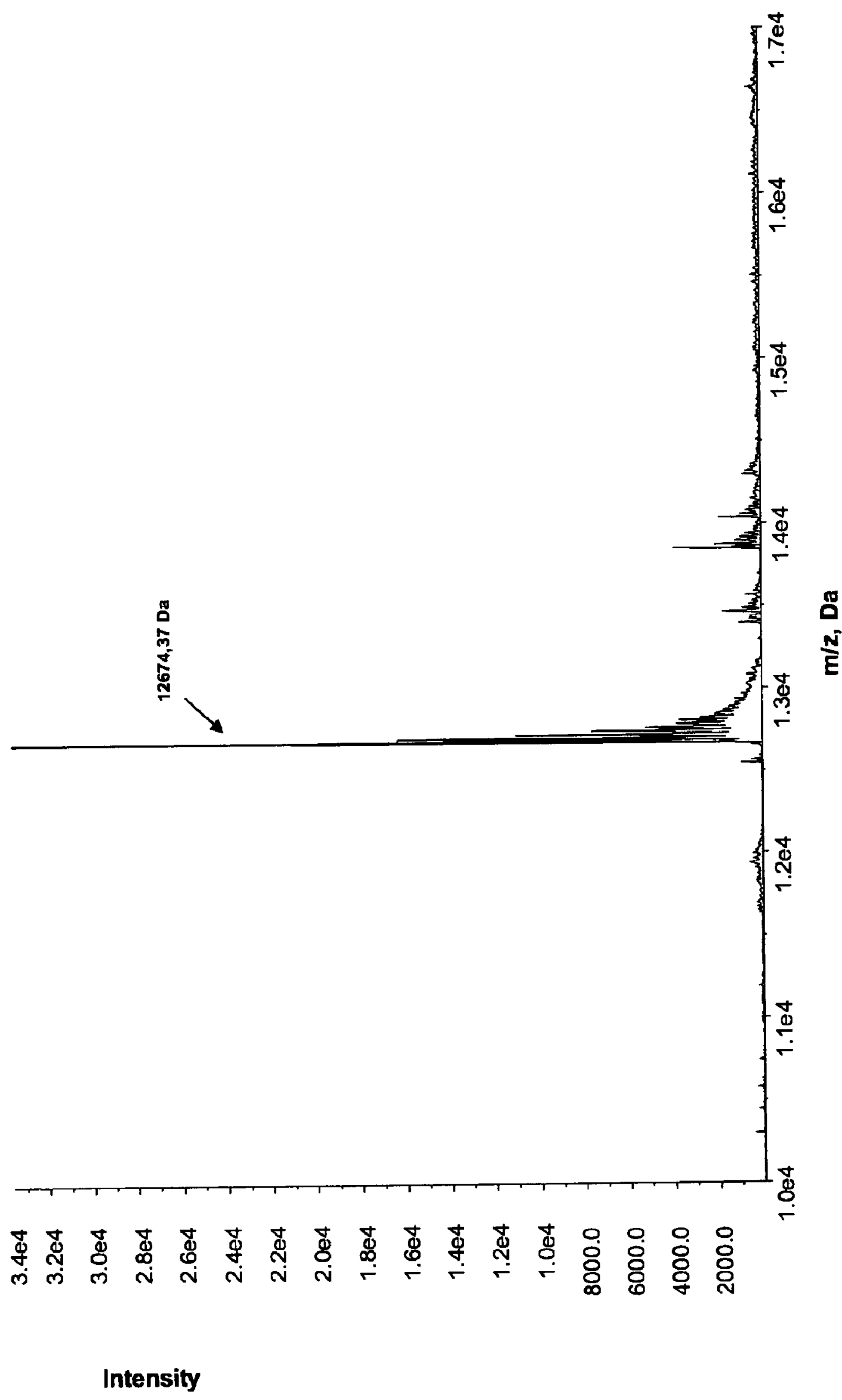
Figure 6D:
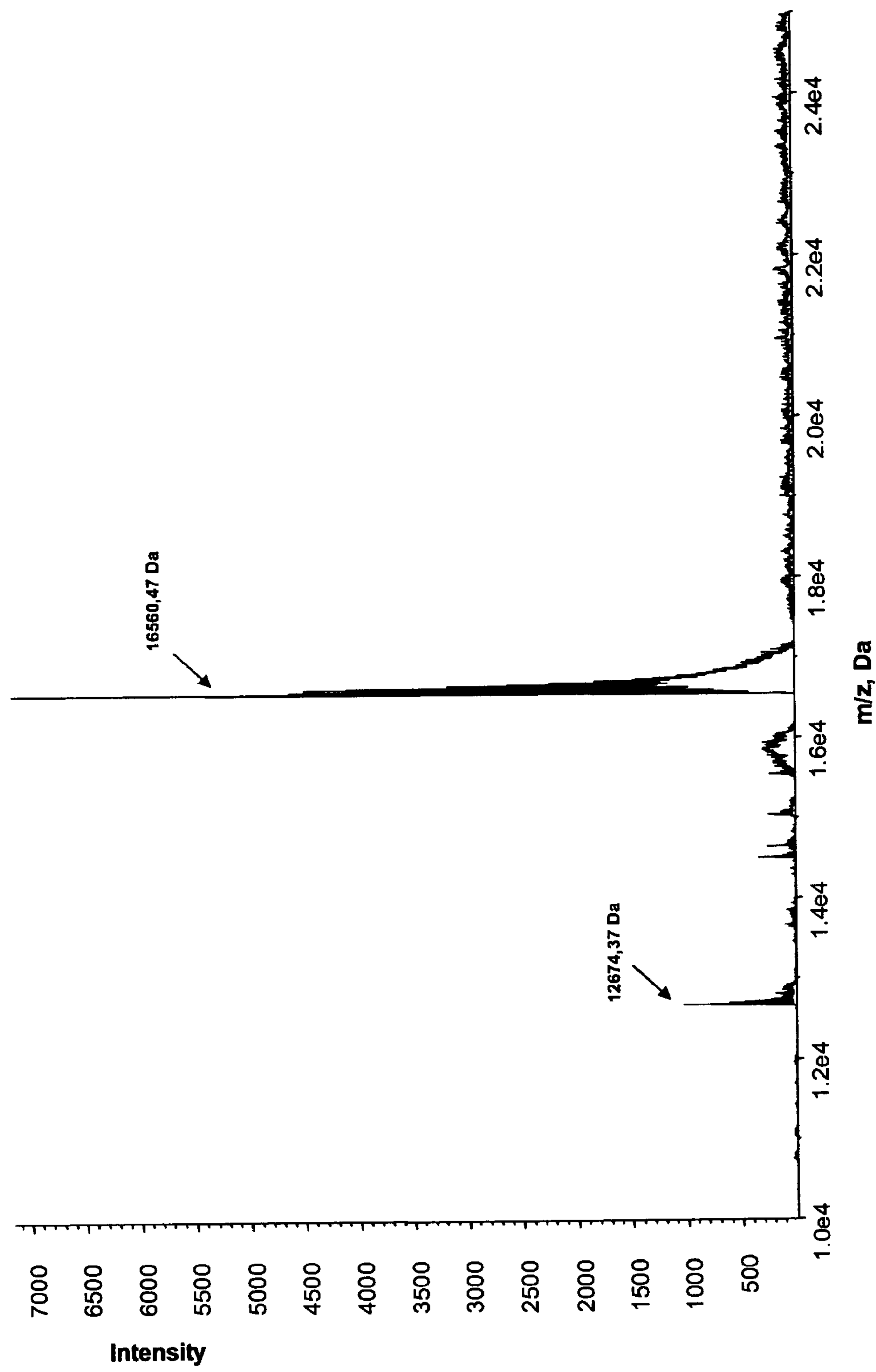

Peak 2 in the TIC chromatogram was clearly the most abundant and the extracted deconvoluted spectrum showed a predominant peak corresponding in mass to the released purification tag (SEQ ID NO:32-SEQ ID NO:16, 12764,84 Da, average isotopic mass, calculated) (FIG. 6C). The extracted deconvoluted spectrum of Peak 3 showed the mass of the intact unprocessed ACSH204 fusion protein (16561,1 Da average isotopic mass, calculated). The peak size of the amylin peptide on the TIC chromatogram does not correspond to the size of the released SEQ ID NO:32-SEQ ID NO:16 tag, which is possibly due to less binding of the peptide to the C8 column, differences in ionization efficiency or aggregation of released amylin after released from the tag.

Our data shows that, it is possible to make human Amylin in soluble form that can purified and processed with EK using basic thermostable purification tags.

The invention claimed is:

1. A method for purification of a recombinant target protein expressed in a eukaryotic or prokaryotic host cell comprising:

(a) isolating an expressed tagged protein from the host cell, wherein the expressed tagged protein comprises a target protein, the purification tag of SEQ ID NO: 24, and a linker sequence comprising a cleavage site for in vitro cleavage of the target protein from the purification tag;

(b) subjecting the expressed tagged protein to cation-exchange chromatography purification;

(c) cleaving the target protein from the purification tag; and (d) isolating the target protein.

2. The method according to claim 1, wherein the linker has from 1 to about 30 amino acid residues.

3. The method according to claim 1, wherein the linker has from 1 to about 15 amino acid residues.

4. The method according to claim 1, wherein the linker comprises amino acid residues selected from the group consisting of Pro, Leu and Ala.

5. The method according to claim 1, wherein the linker comprises a cleavage site which is selected from the group consisting of an enterokinase cleavage site, a Factor Xa cleavage site, a thrombin cleavage site, a Tobacco etcs virus protease cleavage site and a HRV14 3C protease cleavage site.

6. The method according to claim 1, wherein the linker has a peptide sequence of SEQ ID NO: 9.

7. The method according to claim 1, wherein the host cell is selected from bacteria or fungi such as *Eschericia* sp., *Bacillus* sp., *Saccharomyces* sp. and, *Aspergillus* sp.

8. The method according to claim 1 further comprising a heat precipitation step for precipitating thermolabile host cell contaminants before the cation-exchange column in step (b).

9. The method according to claim 1, wherein the target protein is human hGH or an analogue thereof.

10. The method according to claim 9, wherein the target protein is hGH-Leu-Ala or Ser-hGH.

11. The method according to claim 8, wherein from about 30 to about 200 mM NaCl is added before the heat precipitation step.

12. The method of claim 1 wherein cleaving the target protein from the purification tag is accomplished by a suitable processing enzyme.

* * * * *